US010272429B2

(12) United States Patent
Gaige et al.

(10) Patent No.: US 10,272,429 B2
(45) Date of Patent: Apr. 30, 2019

(54) CONNECTORS FOR PNEUMATIC DEVICES IN MICROFLUIDIC SYSTEMS

(71) Applicant: EMD Millipore Corporation, Burlington, MA (US)

(72) Inventors: Terry Gaige, Hayward, CA (US); Andrew Zayac, Hayward, CA (US); Paul Sydlowski, Danvers, MA (US); Philip Lee, Almeda, CA (US)

(73) Assignee: EMD Millipore Corporation, Burlington, MA (US)

( * ) Notice: Subject to any disclaimer, the term of this patent is extended or adjusted under 35 U.S.C. 154(b) by 0 days.

(21) Appl. No.: 15/831,976

(22) Filed: Dec. 5, 2017

(65) Prior Publication Data

US 2018/0093266 A1   Apr. 5, 2018

Related U.S. Application Data

(62) Division of application No. 15/006,765, filed on Jan. 26, 2016, now Pat. No. 9,861,982.
(Continued)

(51) Int. Cl.
*B01L 3/00* (2006.01)
*A61J 1/06* (2006.01)
(Continued)

(52) U.S. Cl.
CPC ..... *B01L 3/50273* (2013.01); *B01L 3/502715* (2013.01); *B01L 3/563* (2013.01);
(Continued)

(58) Field of Classification Search
CPC ................ A61J 1/06; B01L 3/00; B01L 99/00
(Continued)

(56) References Cited

U.S. PATENT DOCUMENTS 4,412,557 A   11/1983   Schmid
5,361,492 A   11/1994   Miyazawa
(Continued)

FOREIGN PATENT DOCUMENTS

DE   3804425 C1   9/1989
DE   10037448 A1   2/2002
(Continued)

OTHER PUBLICATIONS

European communication dated Jul. 14, 2016 in corresponding European patent application No. 16158470.1.
(Continued)

*Primary Examiner* — Brian J. Sines
(74) *Attorney, Agent, or Firm* — Nields, Lemack & Frame, LLC

(57) ABSTRACT

In one embodiment, a removable pneumatic connector, comprises a body having a plurality of bores passing through, each bore surrounded by a sealing member on an inner surface of the body. A plurality of gas lines may be placed within a corresponding bore. A vacuum port is disposed on the inner surface of the body, and an outer seal on the inner surface of the body surrounds the sealing members and the vacuum port.
A vacuum line may be placed within the vacuum port, and configured to deliver negative pressure to the vacuum port. A vacuum holding area is created in the volume between the outer seal and each of the sealing members when the inner surface of the body is placed against a substrate. When the vacuum line is activated, a vacuum is created within the vacuum holding area, creating a positive seal between the body and the substrate.

6 Claims, 17 Drawing Sheets

Related U.S. Application Data

(60) Provisional application No. 62/130,089, filed on Mar. 9, 2015.

(51) Int. Cl.
  *B01L 99/00* (2010.01)
  *C12M 3/06* (2006.01)
  *C12M 1/00* (2006.01)
  *G01N 35/00* (2006.01)

(52) U.S. Cl.
  CPC ............ *C12M 23/16* (2013.01); *C12M 23/40* (2013.01); *G01N 35/00871* (2013.01); *B01L 2200/025* (2013.01); *B01L 2200/027* (2013.01); *B01L 2200/0689* (2013.01); *B01L 2300/0681* (2013.01); *B01L 2300/0861* (2013.01); *B01L 2300/14* (2013.01); *B01L 2300/165* (2013.01); *B01L 2400/049* (2013.01)

(58) Field of Classification Search
  USPC ........ 422/68.1, 81, 501, 502, 503, 537, 538, 422/551, 552, 554, 560, 561, 565, 566, 422/568, 569; 436/43, 174, 180
  See application file for complete search history.

(56) References Cited

U.S. PATENT DOCUMENTS

| | | | |
|---|---|---|---|
| 6,832,787 B1 | 12/2004 | Renzi | |
| 6,926,313 B1 | 8/2005 | Renzi | |
| 7,311,882 B1 | 12/2007 | Renzi | |
| 7,537,730 B2 | 5/2009 | Colin et al. | |
| 9,861,982 B2 | 1/2018 | Gaige et al. | |
| 2002/0042125 A1 | 4/2002 | Petersen et al. | |
| 2002/0114447 A1 | 8/2002 | Ooya et al. | |
| 2008/0139865 A1 | 6/2008 | Galliher et al. | |
| 2009/0121476 A1 | 5/2009 | Malito et al. | |
| 2009/0130745 A1 | 5/2009 | Williams et al. | |
| 2010/0044538 A1 | 2/2010 | Lee | |
| 2011/0104730 A1 | 5/2011 | Larsen et al. | |
| 2012/0025521 A1 | 2/2012 | Bailer et al. | |
| 2016/0263572 A1 | 9/2016 | Gaige et al. | |
| 2016/0312166 A1 | 10/2016 | Lee et al. | |

FOREIGN PATENT DOCUMENTS

| | | |
|---|---|---|
| EP | 0050913 A1 | 5/1982 |
| EP | 054883 A1 | 6/1993 |
| JP | 2002-237351 A | 8/2002 |
| JP | 2004-296426 A | 10/2004 |
| JP | 2005-192753 A | 7/2005 |
| JP | 2009-543553 A | 12/2009 |
| JP | 2010-536348 A | 12/2010 |
| JP | 2015-500020 A | 1/2015 |
| WO | 2008/063070 A1 | 5/2008 |
| WO | 2013/082612 A1 | 6/2013 |

OTHER PUBLICATIONS

Japanese communication, with English translation, dated Feb. 7, 2017 in corresponding Japanese patent application No. 2016-044640.

Japanese communication, with English translation, dated Aug. 21, 2018 in corresponding Japanese patent application No. 2017-152750.

CONNECTORS FOR PNEUMATIC DEVICES IN MICROFLUIDIC SYSTEMS

This application is a divisional of U.S. patent application Ser. No. 15/006,765 filed Jan. 26, 2016, which claims priority of U.S. Provisional Application Ser. No. 62/130,089 filed Mar. 9, 2015, the disclosures of which are incorporation herein by reference.

FIELD OF THE DISCLOSURE

The disclosure generally relates to microfluidic devices and methods for cell culture. In particular, the disclosure relates to connectors used in the pneumatic control of microfluidic devices and cell culture.

BACKGROUND

The ability to grow and maintain cells in vitro was a significant milestone in the biological sciences. However, traditional cell culture techniques lack the ability to analyze single cells, as opposed to bulk cultures. Population-averaged bulk assays are often inaccurate or misleading due to natural cell-to-cell variability. Further, cell signaling and other biochemical parameters constantly change, making dynamic analysis of cells crucial in understanding how a biological system operates. In response to these limitations, microfluidic cell culture systems have been developed that allow for high throughput and multiplexed culture and analysis of individual cells.

Microfluidic cell culture is a promising technology for applications in drug screening, tissue culturing, toxicity screening, and biologic research and can provide improved biological function, higher quality cell-based data, reduced reagent consumption, and lower cost. The most common approach for manufacturing microfluidic devices is soft lithography of polydimethylsiloxane (PDMS), which allows structures of micrometer resolution to be molded from a hard master. PDMS-based culture systems and devices may include a variety of structures, including various kinds of channels, chambers, barriers, and valves. Each of these components may be networked together in various configurations to create a "lab on a chip" device that can be utilized to conduct a variety of biological experiments. Further, microfluidic cell culture systems can be highly multiplexed, allowing for multiple conditions or samples to be tested on a single device.

Key benefits of microfluidic cell culture include improved biological function, higher-quality cell-based data, reduced reagent consumption, and lower cost. Further, high quality molecular and cellular sample preparations are important for various clinical, research, and other applications. In vitro samples closely representing their in vivo characteristics can potentially benefit a wide range of molecular and cellular applications. Handling, characterization, culturing, and visualization of cells or other biologically or chemically active materials (such as beads coated with various biological molecules) have become increasingly valued in the fields of drug discovery, disease diagnoses and analysis, and a variety of other therapeutic and experimental work.

The relatively small scale and multiplexed nature of microfluidic devices results in high applicability to automation. Automated systems are particularly useful in the pharmaceutical industry, which relies on high throughput screening of libraries of chemical compounds to find potential drug candidates. By using microfluidic devices, high throughput screening can test many discrete compounds in parallel so that large numbers of test compounds are screened for biological activity simultaneously. In such systems, pneumatic control is often used to load cells and drive other actions on a microfluidic device. However, imperfect sealing of a pneumatic control system to a microfluidic device may result in improper pressures being applied to the device, thus biasing the results of the analysis. Connections between the pneumatic control system and microfluidic device, such as gas line tubing, may also become contaminated, requiring either disposal, or extensive and manual cleaning.

SUMMARY

The problems of the prior art are addressed by a novel design of a pneumatic connector for interfacing a microfluidic control and analysis system with a microfluidic device. Embodiments of pneumatic connectors according to the disclosure may be in in communication with either end of a tubing, such as 10-line ribbon tubing, used to supply gases, fluids, or other media from a pneumatic control system to a microfluidic device. Pneumatic connectors may be removable and secured using an existing in-line vacuum force provided via the tubing and pneumatic control system. In certain embodiments, the pneumatic connectors may be removable and secured using magnetic force. In still further embodiments, the pneumatic connectors may use mechanical attachment means, such as thumb screws and the like. Pneumatic connectors may simultaneously establish multiple secure connections from a pneumatic control system to a microfluidic device. The connections may be configured to deliver variable pressure to control fluidic flow on the microfluidic device. At least one connection may be configured to deliver negative pressure to create a vacuum. In certain embodiments, pneumatic connectors may be configured to engage with a rigid pneumatic manifold that interfaces with a consumable microfluidic plate designed for live cell culture and imaging. Accordingly, in these embodiments, the vacuum may be used to seal the pneumatic manifold to the microfluidic plate, and also to seal the pneumatic connector to the pneumatic manifold. In still further embodiments, pneumatic connectors may be configured to engage with a pneumatic interface of the pneumatic control system. Further, in certain embodiments, the connector may comprise filters for preventing the backflow of liquids into a controller. Accordingly, the novel design results in a removable, repeatable, and reliable pneumatic connector located directly at a convenient interface between the pneumatic controller and the microfluidic plate. When used in an automated system, embodiments of pneumatic connectors according to the disclosure greatly ease user workflow and substantially reduce the possibility of malfunctions.

BRIEF DESCRIPTION OF THE DRAWINGS

For a better understanding of the present disclosure, reference is made to the accompanying drawings, which are incorporated herein by reference and in which.

DETAILED DESCRIPTION

The detailed description set forth below in connection with the appended drawings is intended as a description of embodiments and does not represent the only forms which may be constructed and/or utilized. However, it is to be understood that the same or equivalent functions and sequences may be accomplished by different embodiments that are also intended to be encompassed within the spirit and scope of the disclosure, such as removable pneumatic connectors and systems using different geometries, materials, number of connections, and other alignment or mounting features in order to facilitate mounting, automation, or simple operator use.

Microfluidic Plate Control and Analysis System

Figure 1:
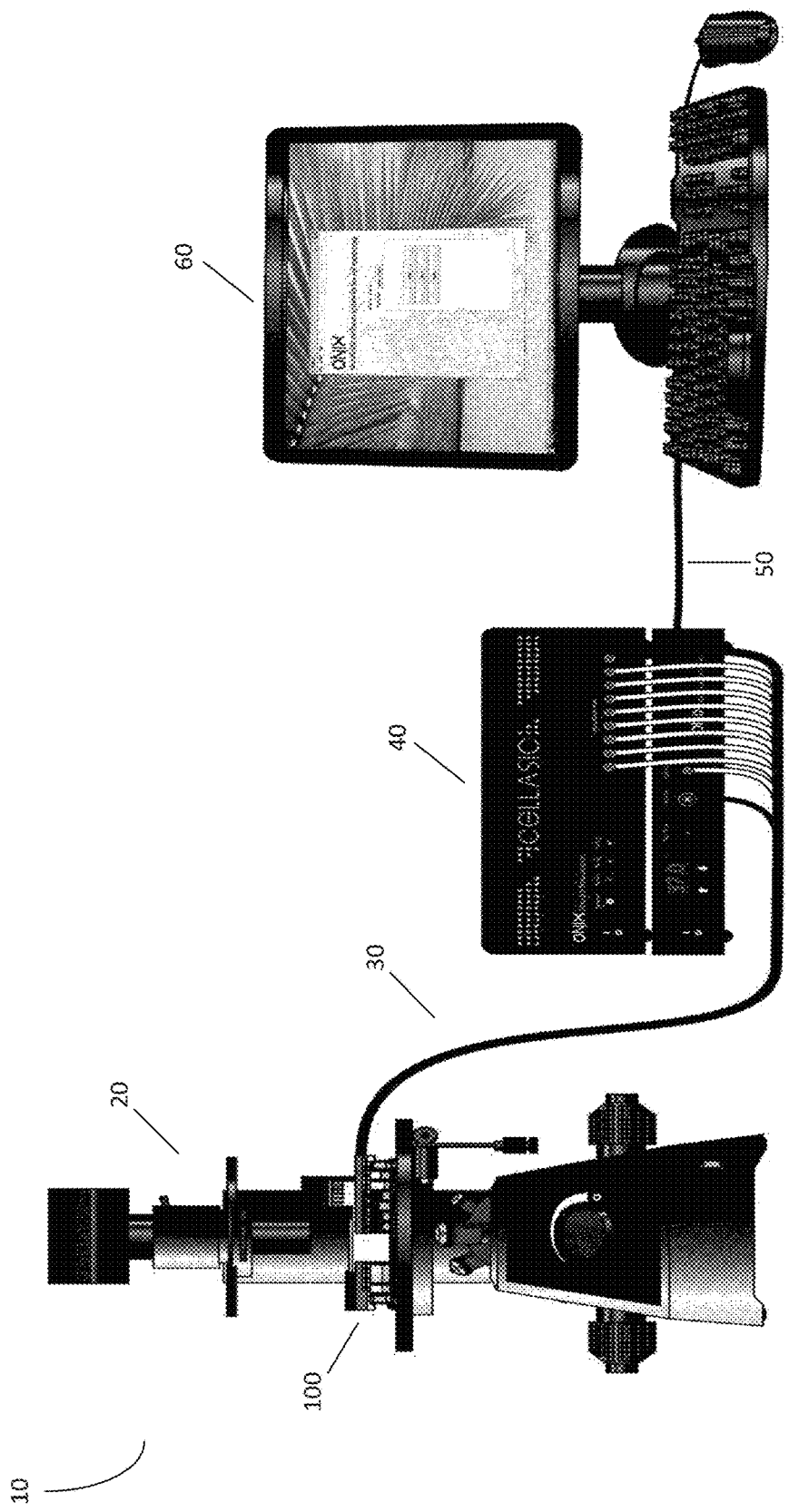
FIG. 1 is a system diagram of an embodiment of a microfluidic control and analysis system according to the disclosure.

Microfluidic cell culture systems provide a powerful tool to conduct biological experiments. FIG. 1 illustrates an embodiment of a microfluidic plate control and analysis system 10 according to the present disclosure. The microfluidic plate control and analysis system 10 comprises a microfluidic plate 100 positioned on the stage of an inverted microscope 20. Cell culture or other processes occurring on the plate 100 may be observed using the inverted microscope 20. The plate 100 is in communication with a pneumatic controller 40 via tubing 30, which may comprise 10-line ribbon tubing. The tubing 30 may also comprise other forms of communication and connections between the pneumatic controller 40 and microfluidic plate 100, such as individual gas line tubing, electrical wiring, heating elements, networking components, and the like. The pneumatic controller 40 may be configured to interact with the microfluidic plate 100 by using the tubing 30 to supply a gas or liquid to the plate 100, control the temperature of the plate 100, or perform other desired functions. The controller 40 is further in communication with a computer 60 via a network connection 50. The computer 60 may be configured to display and/or analyze image data from the microscope 20, record actions taken by the pneumatic controller 40, and instruct the pneumatic controller 40 to take actions according to a protocol.

In this embodiment, the microfluidic plate 100 comprises a glass bottom for imaging, and may be configured to fit within the stage holder of the inverted microscope 20. In certain embodiments, the microfluidic plate 100 has dimensions corresponding to a Society for Biomolecular Screening (SBS) standard 96-well plate. The microfluidic plate 100 may use an application-specific design depending on the type of experiment desired, such as cell culture, solution exchange, or comparison of conditions. In certain embodiments, the microfluidic plate 100 may be a CellASIC® ONIX Microfluidic Plate for Live Cell Analysis, commercially available from EMD Millipore Corporation. Further, the microfluidic plate 100 may be multiplexed, allowing for a single microfluidic plate 100 to perform several individual or related experiments, either simultaneously or sequentially.

The tubing 30 may be configured or utilized for a particular purpose, such as supplying a gas or liquid to the microfluidic plate 100. In this embodiment, the tubing 30 comprises 10-line ribbon tubing configured such that eight of the lines provide variable pressure to the microfluidic plate 100, one line provides a desired gas environment, and one line provides negative pressure to create a vacuum. In certain embodiments, the tubing 30 may further comprise a connection (e.g., an electrical connection) in communication with a heating element or heat exchanger in communication with the microfluidic plate 100, thus incubating the microfluidic plate 100 to a desired temperature. While the embodiments described in this disclosure utilize a 10-line ribbon tubing, various other forms of connections and communication between the pneumatic controller 40 and microfluidic plate 100 may be used, including those of greater or fewer lines, or utilizing other means of delivering pressure, gas, vacuum, and/or heat.

Each line of the 10-line ribbon tubing may be in communication with the controller 40, which may comprise a plurality of ports configured to generate pressure or vacuum, regulate pressure, open or close valves, and/or supply a gas environment (e.g., 5% $CO_2$) having a desired temperature and humidity. The controller 40 may further comprise a heating controller that instructs a corresponding heating element in communication with the microfluidic plate 100 to raise or lower the temperature of the microfluidic plate 100. For example, the heating controller may be configured to maintain the temperature of the microfluidic plate at 37° C., mimicking in vivo conditions. In this embodiment, the controller 40 is a CellASIC® ONIX Microfluidic Control System (commercially available from EMD Millipore Corporation), which is able to supply positive pressure up to 10 PSI and negative pressure of −8.2 PSI. However, any suitable controller that is able to provide any of variable pressure, a desired gas environment, or temperature control for a microfluidic device may be used.

The computer 60 is in communication with the controller 40 over a network connection 50. In this embodiment, the network connection 50 comprises a USB connection. However, the network connection 50 may be any form of connection enabling communication between the controller 40 and computer 60, including serial, parallel, and Ethernet connections. Further, in certain embodiments, the controller 40 and computer 60 may comprise a single unit. In this embodiment, the network connection 50 may be an integral component.

In this embodiment, the computer 60 includes software configured to manage various aspects of the microfluidic plate control and analysis system 10. The computer 60 may be configured to operate the controller 40 according to a protocol for an experiment. For example, the computer 60 can send control signals to the controller 40 instructing the controller 40 to provide variable pressure to the microfluidic plate 100, or take other actions, according to a either a pre-determined or dynamic schedule. Further, the computer 60 may be configured to receive user input and modify protocols, including the ability to set flow sequences, set desired pressures, or store programs and protocols. The computer 60 may also be used to determine the overall system status. However, in certain embodiments, these features may also be implemented wholly or partly within the controller 40.

In certain embodiments, the computer 60 may further be in communication with a digital camera attached to the inverted microscope 20. In these embodiments, the computer 60 may include the capability to display, monitor, and track images captured by the digital camera of the microfluidic plate 100. This feature is particularly useful for long-term live cell analyses, wherein processes may take days and interesting events may occur during off hours. Further, in larger automated systems, this feature can be used to track conditions at designated time points for a plurality of samples without a need for human intervention.

Microfluidic Culture Plate

Figure 2:
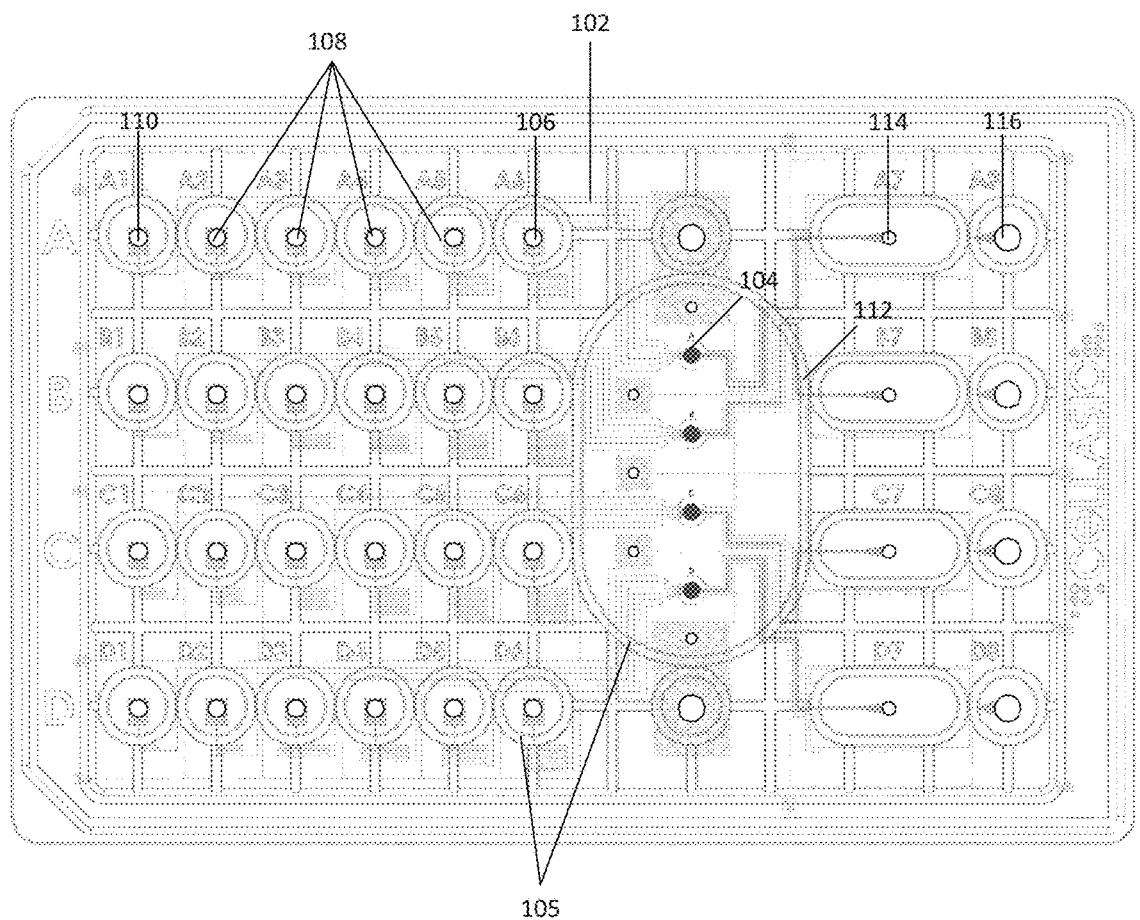
FIG. 2 is a top view of an embodiment of a microfluidic plate within the microfluidic control and analysis system of FIG. 1.

FIG. 2 illustrates the microfluidic plate 100 within the microfluidic control and analysis system 10 of FIG. 1 in further detail. In this embodiment, the microfluidic plate 100 may be PDMS-based and may comprise a plurality of independent assay units (i.e., the 4 rows labeled "A"-"D"). Each assay unit may comprise a plurality of fluidic channels 102 in communication with a culture chamber 104. Cells or other fluids may be loaded into the culture chamber 104 via a cell inlet well 106 (e.g., the well labeled "A6"). Further, various solutions or reagents may be provided to the culture chamber 104 via a plurality of solution inlet wells 108 ("A2"-"A5") and a gravity perfusion well 110 ("A1"). A viewing window 112 is formed over the culture chamber 104, allowing for placement of the lens of a microscope (e.g., the inverted microscope 20 of FIG. 1) to view the cells or other processes taking place within. Each assay unit may further comprise a waste outlet well 114 ("A7") for waste from the culture chamber 104, and a perfusion outlet well 116 ("A8") for waste from the solution inlet wells 108 and gravity perfusion well 110.

A plurality of sidewalls 105 extending upward from the plate 100 are formed around the wells, culture chamber 104, and viewing window 112, isolating these features from one another. At least some of the sidewalls 105 extend to the top of the plate 100, such that placing a manifold over the plate 100 results in the sidewalls 105 being in contact with the manifold. As will be described further below, this feature may be used to deliver isolated pneumatic pressure to each well via a pneumatic manifold, provide a desired gas environment to the culture chambers 104, or create a vacuum within other areas of the plate 100.

Figure 3:
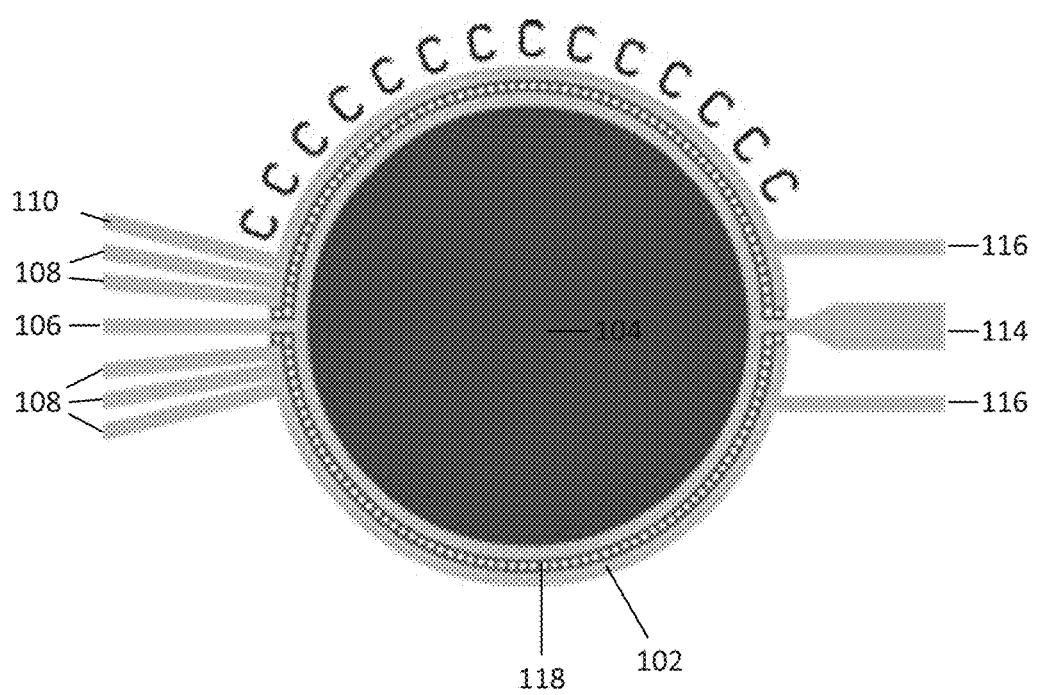
FIG. 3 is a diagram depicting an embodiment of a cell culture area within the microfluidic plate of FIG. 2.

FIG. 3 illustrates the culture chamber 104 in further detail. The cell inlet well 106 is in direct communication with the culture chamber 104, allowing for free flow of cells from the cell inlet well 106 into the culture chamber 104. In contrast to the cell inlet well 106, the fluidic channels 102 connecting the solution inlet wells 108 and gravity perfusion well 110 are separated from the culture chamber 104 by a perfusion barrier 118. In this embodiment, the perfusion barrier 118 is a combination of solid structures and passages smaller than the fluidic channels 102 that separates the fluidic channels 102 from the culture chamber 104. The perfusion barrier 118 is designed to keep cells, other culture items, and gels from migrating into the fluidic channels 102, while allowing some fluidic flow through diffusion, perfusion, or any combination of mass transfer mechanisms that is generally of a much higher fluidic resistance than the fluid flow in the flow channels. In this way, media and reagents can be supplied to the culture chamber 104 without the risk of blocking the fluidic channels 102.

The microfluidic plate 100 is prepared for use by first priming the fluidic channels 102 with a desired buffer, such as sterile PBS. Next, 10 μL of a desired cell suspension is pipetted into the cell inlet well 106. Aspirating the waste outlet well 114 causes the cell suspension to load into the culture chambers 104 through capillary action. Once in the culture chamber 104, cells may be perfused with media supplied to the gravity perfusion well 110, or exposed to reagents or other chemicals supplied to any of the solution inlet wells 108. As the plate 100 includes four independent assay units, up to four different samples of cells may be independently cultured on a single plate 100. The status of cell culture and response may be observed, for example, by viewing each culture chamber 104 through the viewing window 112 with a microscope.

Once cells are sufficiently cultured, a variety of experiments may be conducted using the microfluidic plate 100. For example, the solution inlet wells 108 can be used for solution switching experiments, wherein cells are sequentially exposed to various solutions and the resulting cellular response is analyzed. To expose cells within the culture chamber 104 to a desired solution, an amount of that solution (e.g., 10 μL) is pipetted into a solution inlet well 108 (e.g., A2). The solution then traverses the fluidic channels 102 and perfuses through the perfusion barrier 118 and into the culture chamber 104. Subsequently, the cells may be exposed to other solutions via the other solution inlet wells and similarly observed. In addition to solution switching, the solution inlets may also be used for automated staining and washing protocols, and on-demand fixation by flowing fixative into the culture chamber 104 during imaging.

Further, it should be noted that while the present disclosure refers to pneumatic control of the microfluidic plate 100, embodiments of the disclosure may be used for any form of microfluidic device, plate, or control and analysis system. Various embodiments are considered to be within the scope of the disclosure.

Pneumatic Manifold

Simple gravity-driven perfusion may be used to both culture cells and expose cells to various reagents. While gravity-driven perfusion allows for an operator to conduct an experiment using only a microfluidic plate 100 without any additional hardware (e.g., the controller 40 and/or computer 60), it lacks a degree of fine control and also requires continuous monitoring by an operator. Accordingly, pneumatic control by way of a pneumatic manifold 120, as in the embodiment shown in FIGS. 4A-B, may also be used to control loading of cells and reagents on the microfluidic plate 100. The pneumatic manifold 120 may be mated to the microfluidic plate 100 in order to finely control cell loading, perfusion of media, and solution exposure by providing variable pressure to each of the wells of the microfluidic plate 100.

Figures 4A, 4B:
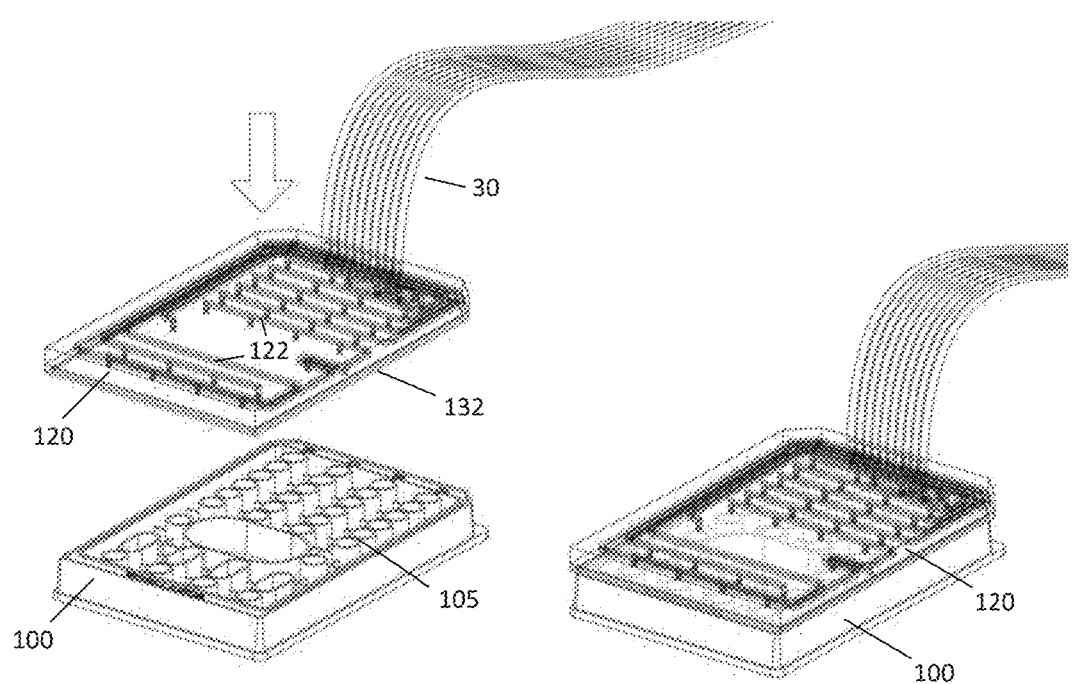
FIGS. 4A-B are perspective views of an embodiment of a pneumatic manifold according to the disclosure as it is positioned onto the microfluidic plate of FIG. 2.

FIGS. 4A-B illustrate the placement and sealing of the pneumatic manifold 120 to the microfluidic plate 100. The manifold 120 may comprise a cyclic olefin copolymer body configured to be positioned over the microfluidic plate 100 and further comprises a plurality of channels 122 which may be used to supply a gas or liquid or deliver negative pressure to the microfluidic plate 100. Each of the channels 122 is in communication with the tubing 30, which as described above may comprise 10-line tubing in communication with a suitable pneumatic controller (such as the pneumatic controller 40 of FIG. 1). The manifold 120 further comprises a soft gasket 132, which should first be cleaned, e.g., with 70% ethanol, and then blotted dry. The plate 100 is then positioned on a flat surface, and the manifold 120 is aligned and set over the wells, as shown in the embodiment of FIG. 4B. Once in place, negative pressure is supplied to at least one of the channels 122 (via one of the gas lines of the tubing 30) such that a vacuum is created between the microfluidic plate 100 and pneumatic manifold 120. As the vacuum is created, an operator (or automated instrument) may press the manifold 120 against the plate 100 for several seconds to ensure uniform contact of the gasket 132. A proper seal forms as the volume between the wells, sidewalls 105, plate 100, and manifold 120 becomes a vacuum. Once a proper seal has been formed, the vacuum should be maintained by an appropriate negative pressure (e.g., −8.2 PSI) to maintain a positive seal and vacuum throughout the course of the experiment. In certain embodiments, the pneumatic manifold 120 may be an F84 Manifold for CellASIC® ONIX, commercially available from EMD Millipore Corporation.

Figure 5:
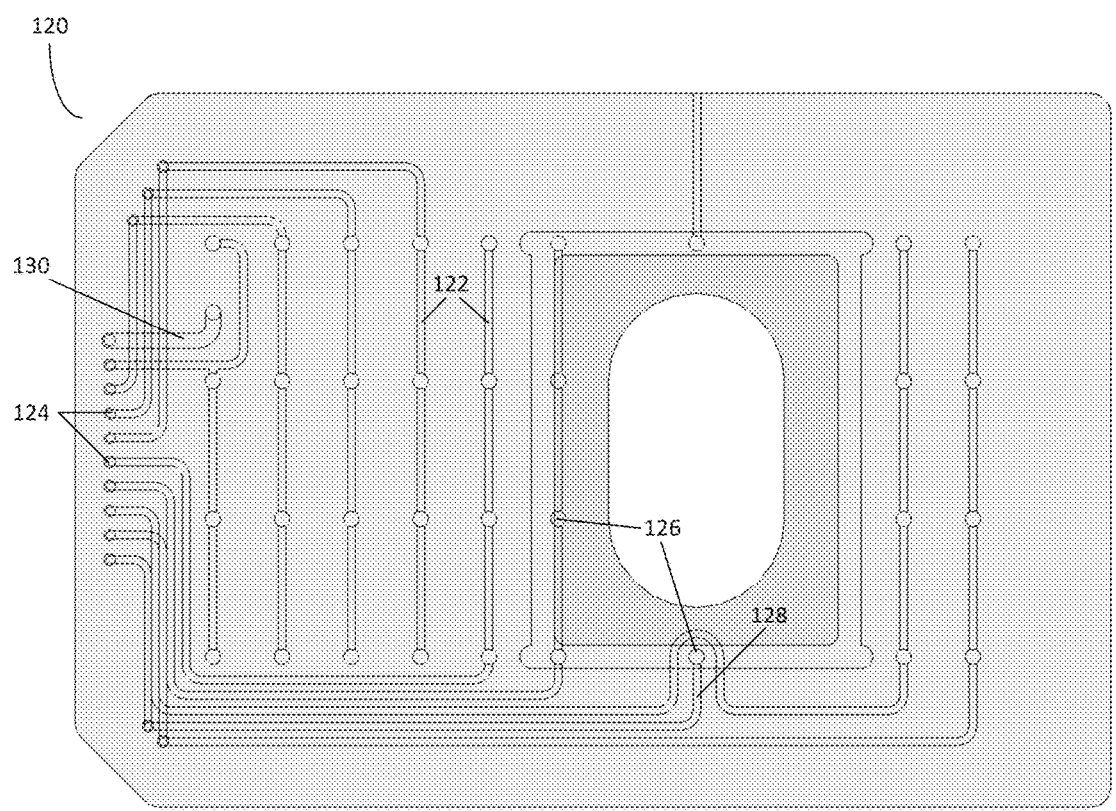
FIG. 5 is a top view of the pneumatic manifold of FIGS. 4A-B.

FIG. 5 illustrates the pneumatic manifold 120 and plurality of channels 122 in further detail. In the embodiment shown, each channel 122 includes a channel inlet 124 on a top side of the manifold 120, which is in communication with a respective gas line, e.g., a line from the 10-line ribbon tubing comprising the tubing 30 of FIG. 1. Each channel 122 is further in communication with at least one channel outlet 126 located on a bottom side of the pneumatic manifold 120. Each channel outlet 126 is positioned such that when the pneumatic manifold 120 is positioned over the microfluidic plate 100, each channel outlet 126 is positioned over a particular well (e.g., the wells of the microfluidic plate 100 of FIG. 2). Further, the sidewalls 105 of the microfluidic plate 100 are in contact with the underside of the manifold 120, thus isolating each channel outlet 126 such that it is only communication with a single well or area of the microfluidic plate 100.

In this embodiment, the pneumatic manifold 120 is configured with sufficient channels 122 and channel outlets 126 to match the number of wells and assay units on the plate 100. Eight of the channels 122 (i.e., the channels 122 labeled "V1"-"V8") include four channel outlets 126, corresponding to the four independent assay units of the microfluidic plate 100 of FIG. 2. Thus, a single channel inlet 124 can be used to apply pressure to a particular well of four assay units on the microfluidic plate 100, controlling flow rates through the fluidic channels 102 of the microfluidic plate 100. However, in certain embodiments, the number and location of channels 122, channel inlets 124, and channel outlets 126 may be varied to match the configuration of a particular microfluidic plate or control system or other needs for an experiment.

The plurality of channels 122 may further comprise a gas environment channel 128, which includes a channel outlet 126 positioned over the viewing window 112 and culture chambers 104 (as shown in FIG. 2). The gas environment channel 128 can be used to provide atmospheric control for the microfluidic plate 100 and bathe cells in the culture chamber 104 with a specified gas environment. As previously described, the microfluidic plate 100 comprises a gas-permeable device layer (i.e., PDMS) over a glass bottom. Thus, gases provided to the microfluidic plate 100 can be delivered to the culture chambers 104 through the gas-permeable device layer by diffusion. In certain embodiments, the gas delivered via the gas environment channel 128 comprises 5% $CO_2$; however, any gaseous mixture, such as mixtures including oxygen and/or nitrogen, may be used. By continuously flowing gas through the gas environment channel 128, a stable gas environment for culturing cells within the culture chambers 104 is maintained. Thus, the gas environment channel 128 provides a means for controlling the environment within the culture chambers 104 other than placing the microfluidic plate 100 into an incubator. This results in the manifold 120 becoming a "micro-incubator," independent of the ambient air, allowing continuous medium perfusion and preventing evaporation.

The plurality of channels 122 may further comprise a vacuum channel 130. The channel outlet 126 for the vacuum channel 130 is positioned in an area between the wells and sidewalls 105 of the microfluidic plate 100. Thus, supplying negative pressure to the vacuum channel 130 when the manifold 120 is positioned over the microfluidic plate 100 creates a vacuum in the volume between the wells, sidewalls 105, manifold, and the microfluidic plate 100, thus sealing the manifold 120 to the plate 100.

Thus, by using the pneumatic manifold 120, pressure can be applied to individual wells to drive cell loading, solution switching, or perfusion of media. Cells may be incubated with a suitable gas environment, and a vacuum ensures that the manifold 120 remains sealed to the microfluidic plate 100. Further, connecting the channel inlets 124 to a controller and corresponding computer (such as the controller 40 and computer 60 of FIG. 1) can be used to automate various protocols and experiments running on the microfluidic plate 100.

As noted above, in this embodiment, the tubing 30 comprises a gas line ribbon tubing having ten lines: eight for pressure control, one for atmosphere, and one for vacuum. However, various numbers and types of connections may be utilized according to embodiments of the disclosure. For example, in certain embodiments, the tubing 30 may provide a liquid to a microfluidic plate 100 or other device. In certain embodiments, the tubing 30 may provide both liquid and pressure control lines, or provide temperature control for the microfluidic plate 100.

Connections Between the Manifold and the Controller

As noted above, the tubing 30 connecting the manifold 120 and the controller 40 may comprise a plurality of gas lines, such as 10-line ribbon tubing. In certain embodiments, the tubing 30 may be permanently connected to both the pneumatic controller 40 and the manifold 120. The tubing 30 may also be removable from either the pneumatic controller 40 or manifold 120, or both, by a variety of mechanisms, including by pneumatic, magnetic, mechanical attachment, and the like.

A. First Embodiment of a Removable Pneumatic Connector

Figure 6:
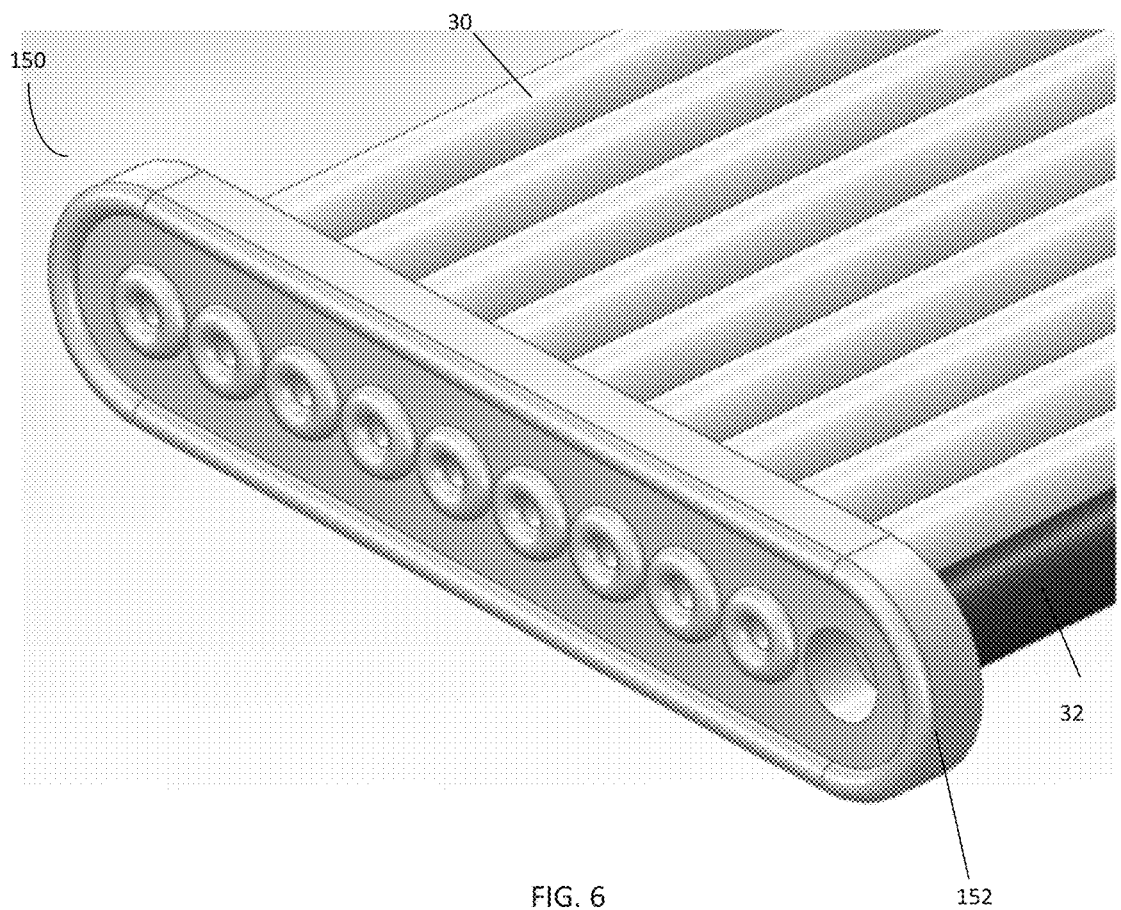
FIG. 6 is a perspective view of an embodiment of a pneumatic connector according to the disclosure.

FIG. 6 illustrates an embodiment of a pneumatic connector 150. The pneumatic connector 150 may be used as an attachment mechanism for removably securing the tubing 30 to a pneumatic manifold, such as the pneumatic manifold 120 of FIG. 5. While in this embodiment, the pneumatic connector 150 is positioned between the tubing 30 and manifold 120, in certain embodiments the pneumatic connector 150 may be positioned between the tubing 30 and the controller 40. In still further embodiments, pneumatic connectors 150 may be situated at both positions.

In this embodiment, the pneumatic connector 150 uses an existing vacuum line 32 on the tubing 30 to removably secure the pneumatic connector 150 to the manifold 120. However, in certain embodiments, the pneumatic connector 150 may use alternate lines separate from the tubing 30 for delivering vacuum or negative pressure to removably secure the connector 150.

Figure 7:
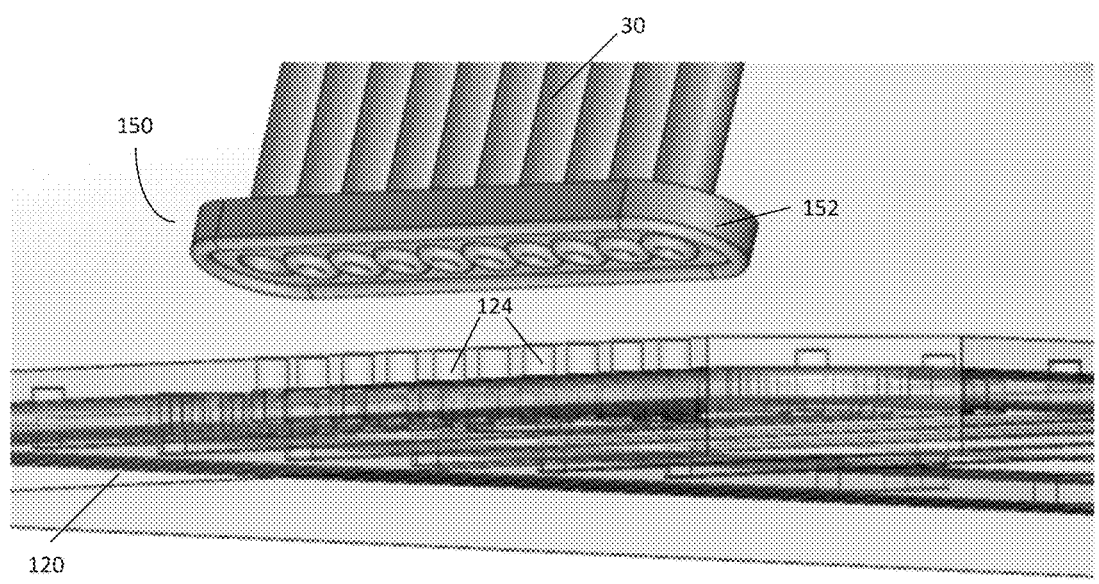
FIG. 7 is a perspective view of the pneumatic connector of FIG. 6 and the pneumatic manifold of FIG. 5.

The pneumatic connector 150 may comprise a body 152 in communication with tubing 30, such as the 10-line ribbon tubing in communication with a pneumatic controller (such as the controller 40 of FIG. 1). In the embodiment shown, the body 152 comprises clear PDMS molded onto a polycarbonate sheet. The pneumatic connector 150 may be configured to be positioned onto the surface of a pneumatic manifold 120 having a corresponding interface as a substrate, such that each gas line of the tubing 30 is in communication with a respective channel inlet 124 on the manifold 120 (as shown in the embodiment of FIG. 7). In this embodiment, the body 152 comprises a rounded rectangular shape. However, a variety of other shapes may be used to accommodate various configurations of tubing 30 and a corresponding interface and substrate according to various embodiments of the disclosure.

Figure 8:
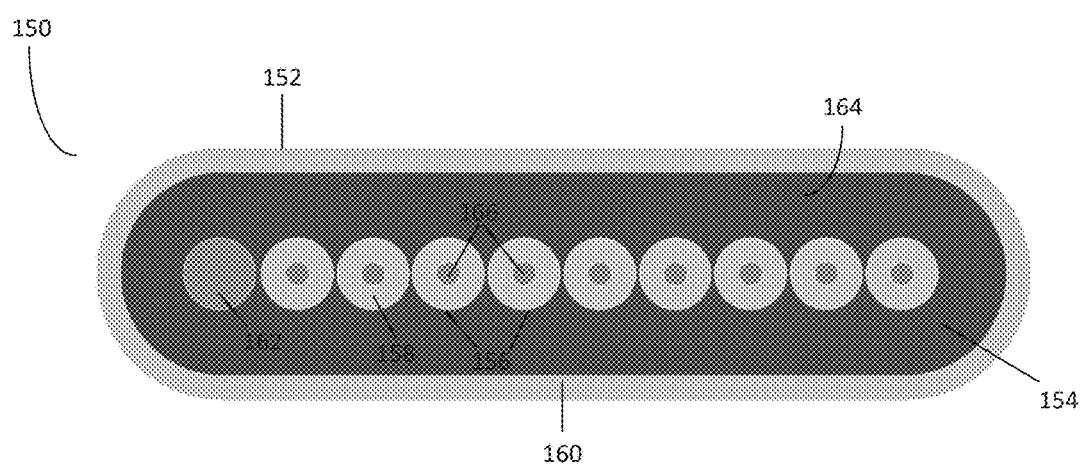
FIG. 8 is a front view of the pneumatic connector of FIG. 6.

FIG. 8 illustrates various aspects of the pneumatic connector 150 in further detail. The body 152 of the pneumatic connector 150 comprises an inner surface 164 that is configured to be placed onto a corresponding substrate, such as the channel inlets 124 on the pneumatic manifold 120 of FIG. 5. The body 152 of the pneumatic connector 150 further comprises a plurality of bores 156 passing through the body 152 such that the bores 156 are exposed to the inner surface 164. Some of the bores 156 may be surrounded by sealing members, such as seals 158. The inner surface 164 may further comprise an outer seal 160 which surrounds each of the bores 156. In this embodiment, at least one of the bores 156 is utilized as a vacuum bore or vacuum port 162, which lacks a corresponding seal 158.

Each of the bores 156 is in communication with a corresponding gas line from the tubing 30. As previously described, the tubing 30 in this embodiment comprises ten gas lines: pressure controlled lines 1-8, a gas environment line, and a vacuum line. Each gas line is placed within a corresponding bore 156. Whereas each bore 156 for the pressure controlled lines and gas environment line includes a corresponding seal 158, the vacuum line placed within the vacuum port 162 does not have a seal.

Placing the connector 150 against a corresponding interface or surface on the pneumatic manifold 120 causes the seals 158 and outer seal 160 to come into contact with that substrate. When placed against such a substrate, a vacuum holding area 154 is formed. The vacuum holding area 154 comprises a space or volume having edges defined by the outer seal 160, inner seals 158, the inner surface 164, and the corresponding substrate against which the connector 150 is placed. Further, the inner seals 158 create a fluid tight separation between each gas line within each bore 156. However, because the vacuum port 162 does not include a seal 158, the vacuum port 162 is in fluid communication with the vacuum holding area 154. Thus, supplying negative pressure to the vacuum port 162 (e.g., via tubing 30 in communication with the controller 40 of FIG. 1) creates a vacuum within the vacuum holding area 154. Accordingly, the difference in pressure between the outside environment and the vacuum holding area 154 seals the pneumatic connector 150 to the surface, creating a secure connection that can be actuated by deactivating and activating the vacuum line in communication with the vacuum port 162.

Figure 9A:
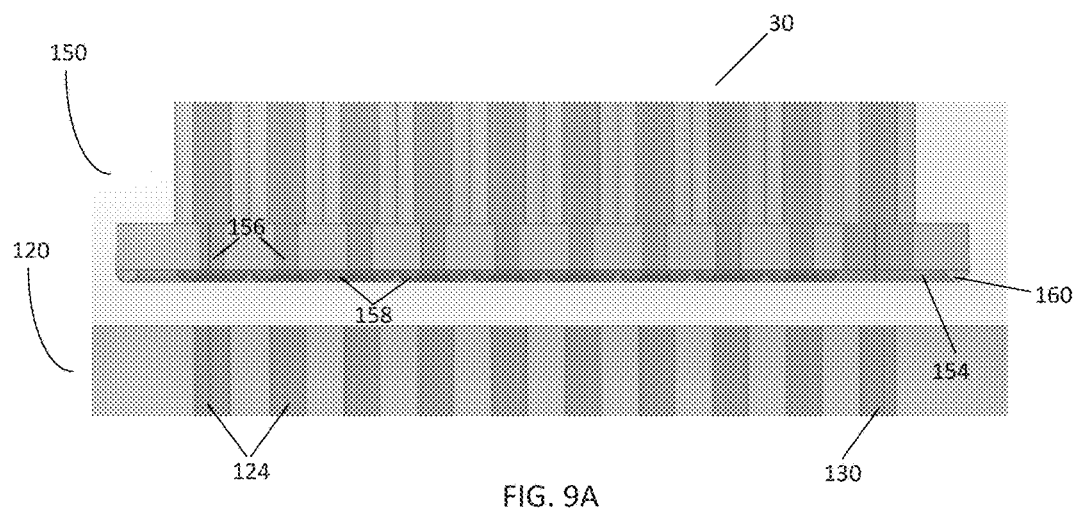
FIGS. 9A-B are cross-sectional views of the pneumatic connector of FIG. 6 and the pneumatic manifold of FIG. 7 as the pneumatic connector is placed in communication with the pneumatic manifold.
Figure 9B:
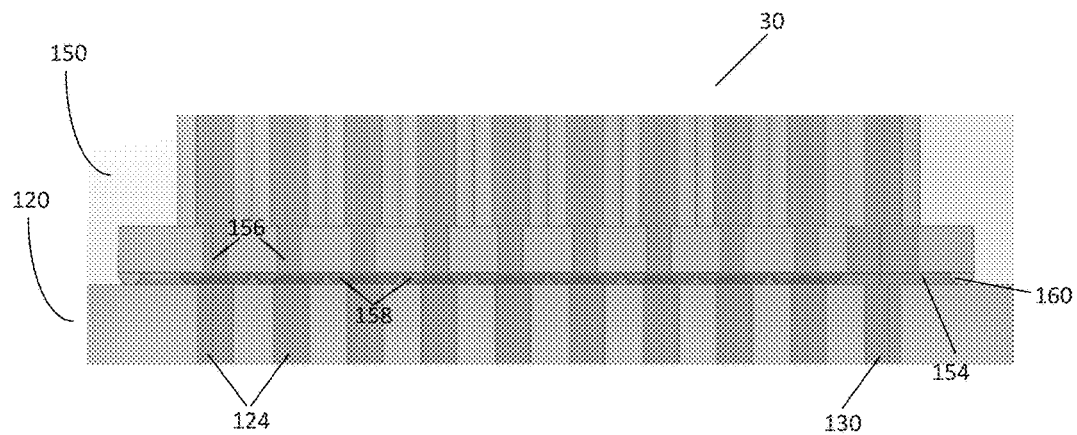

FIGS. 9A-B illustrate the pneumatic connector 150 as it is placed against a manifold 120. In use, the pneumatic connector 150 is placed against the channel inlets 124 of the pneumatic manifold 120. Each of the bores 156 are configured to be positioned over a corresponding channel inlet 124. Actuating the pneumatic connector 150 by creating a vacuum within the vacuum holding area 154 thus places each gas line of the tubing 30 in communication with a respective channel inlet 124. The seals 158 substantially prevent communication between each channel inlet 124, minimizing any cross-talk or leakage between channels. Further, in this embodiment, the pneumatic manifold 120 also includes the vacuum channel 130. Thus, creating a vacuum in the vacuum holding area 154 further supplies a vacuum to the vacuum channel 130 via its corresponding channel inlet 124, sealing the manifold 120 to a microfluidic plate. In this way, the pneumatic connector 150 is able to utilize an existing vacuum line to both hold the pneumatic connector 150 in place against the pneumatic manifold 120, and simultaneously secure the pneumatic manifold 120 to the microfluidic plate. Once secured, the connector 150 may then be used to deliver variable pressure, gas, liquid, or a specified gas environment to various components of the microfluidic plate.

In this embodiment, the seals 158 may comprise O-rings, and the outer seal 160 may comprise a gasket, each of which have a similar thickness, height, and compressibility ratio. However, in certain embodiments, other kinds of seals may be used, provided that the seals sufficiently prevent fluid communication between the bores 156 and thus prevent any leakage between the gas lines of the tubing 30. Further, other kinds of seals may be used provided that a suitable vacuum holding area 154 is created that can sustain vacuum to secure the connector 150 to the manifold 120. Ideally, the choice of seals 158 should result in low leak rates, such as less than 0.1 mL/minute when the gas lines are delivering 10 PSI and the vacuum line is held at −8.2 PSI. While in this embodiment, the tubing 30 comprises ten lines including one vacuum line, in other embodiments, various numbers and combinations of lines may be used, provided that the combination results in a secure connection to the manifold 120.

As described above, in use, the pneumatic connector 150 is placed against the pneumatic interface 134 and the vacuum is activated. Alternately, the vacuum may be activated prior to placing the pneumatic connector 150 against the pneumatic interface 134. The active vacuum line readily grips, holds, and compresses the seals 158 and the outer seal 160 against the substrate of the manifold 120, drawing the connector 150 towards the substrate of the manifold, creating a fluid tight seal and establishing a confident connection of all pressure lines, substantially reducing any leakage or "cross-talk." Due to the vacuum holding area 154, seals 158, and outer seal 160, the pneumatic connector 150 allows for variable connector alignment and consistent sealing, independent of the skill of the operator. Further, misalignment can be detected by a drop in pressure or inability to provide pressure or gas to any of the corresponding channel inlets 124. This detection may be made by a controller or computer in communication with the tubing 30, such as the controller 40 or computer 60, respectively, of FIG. 1.

Figure 10:
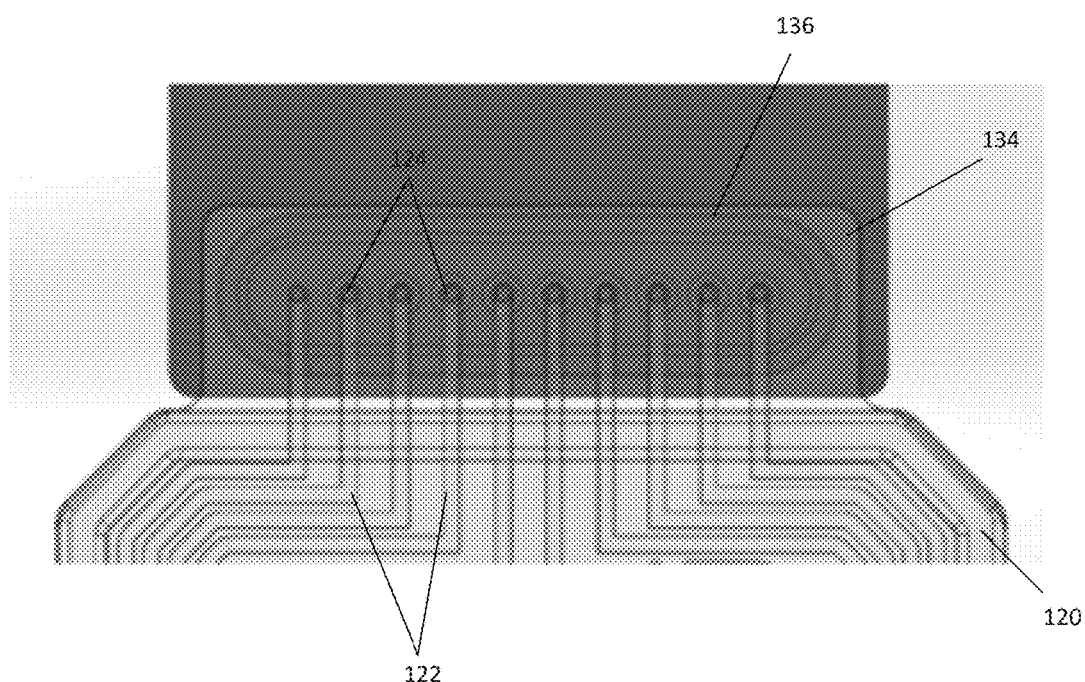
FIG. 10 is a top view of an embodiment of a pneumatic interface for receiving a pneumatic connector located on an embodiment of a pneumatic manifold according to the disclosure.

In certain embodiments, the manifold 120 may comprise additional features to aid proper alignment of the connector 150 to the manifold 120 and channel inlets 124. FIG. 10 illustrates an embodiment of a pneumatic manifold 120 for use with the pneumatic connector 150 that includes a pneumatic interface 134. In this embodiment, the pneumatic interface 134 comprises a tab extending from the pneumatic manifold 120 including the channel inlets 124 in communication with the channels 122, gas environment channel 128, and vacuum channel 130 of the pneumatic manifold 120. The pneumatic interface 134 may also comprise an alignment mechanism 136 for proper alignment, such as a notch or ridge shaped to receive the pneumatic connector 150 and to hold it in place when it is positioned over the pneumatic interface 134. However, in certain embodiments, the pneumatic interface 134 may simply comprise the plurality of channel inlets 124 without any additional features (e.g., the embodiment shown in FIG. 5).

Figure 11A:
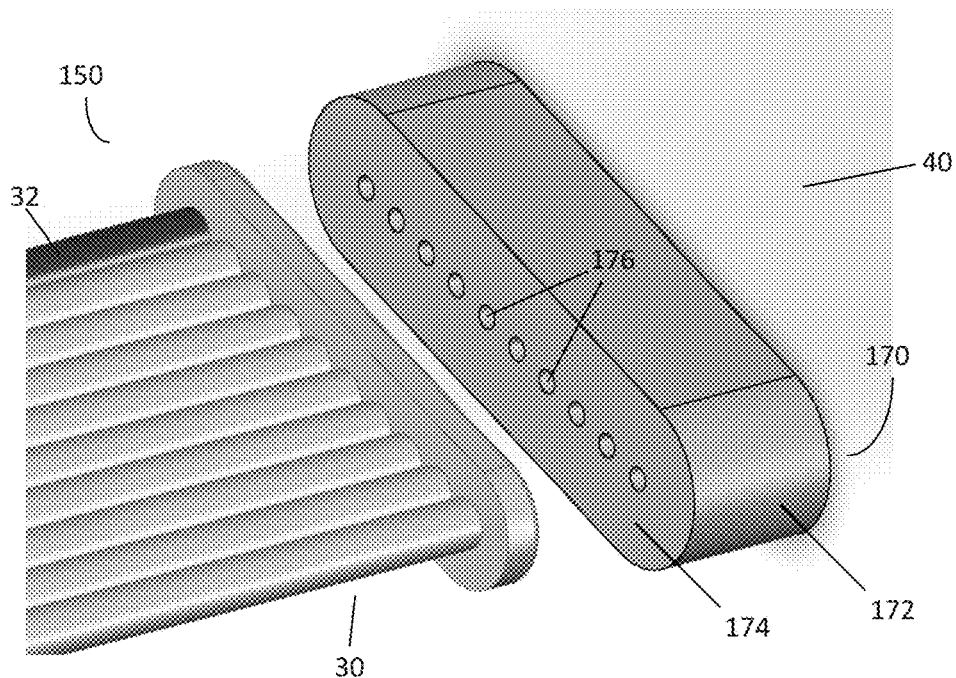
FIGS. 11A-B are perspective views of another embodiment of a pneumatic interface located on a pneumatic control system for receiving the pneumatic connector of FIG. 6.
Figure 11B:
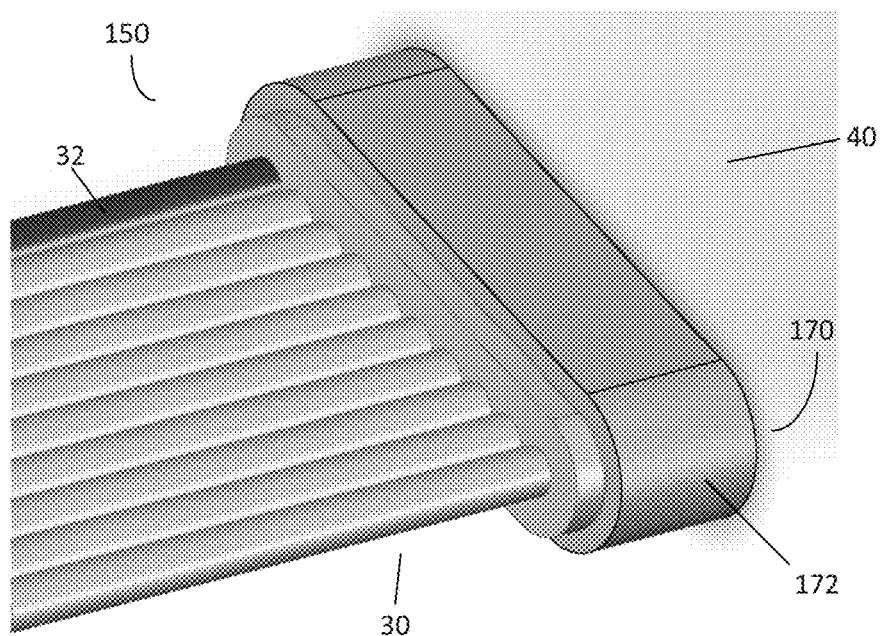

FIGS. 11A-B illustrate another embodiment of a pneumatic interface 170 for use with a pneumatic connector 150. The pneumatic interface 170 may be located either between the manifold and tubing, or between the controller and tubing. In this embodiment, the pneumatic interface 170 is connected to a pneumatic controller, such as the controller 40 of FIG. 1. As shown, the pneumatic interface 170 comprises a body 172 having a mating surface 174 comprising a plurality of channel inlets 176 in communication with channels within the controller 40. The body 172 and mating surface 174 further comprise a rounded rectangle shape so as to accommodate placement of the pneumatic connector 150. In use, the pneumatic connector 150 is placed over the interface 170 such that the vacuum line 32 of the tubing 30 is in communication with a respective vacuum channel of the interface 170. The vacuum line 32 is then activated, securing the connector 150 to the interface 170 in the manner as described above.

In certain embodiments, the microfluidic plate 100 or pneumatic manifold 120 may not include a vacuum channel 130. Thus, in these embodiments, a pneumatic connector 150 according to the disclosure may comprise a vacuum port 162 that is not in communication with a vacuum channel 130 of the manifold 120. In these embodiments, the vacuum port 162 serves only to secure the connector 150 to the manifold, thus placing each bore 156 in communication with a respective channel inlet 124.

The pneumatic connector 150 results in a variety of advantages. For example, the pneumatic connector 150 allows for the manifold 120 to be easily cleaned, or even to be used as a plate lid or cover during sample transfer within labs. Because the pneumatic connector 150 utilizes the existing vacuum line to hold itself in place during use, no additional or pneumatics are required. Thus, the pneumatic connector 150 can utilize pre-existing hardware that can also be used to control a manifold having an umbilical-style, or permanent, connection. Further, by establishing a near-automatic holding force, the pneumatic connector 150 eases operator workflow and reduces the chances of malfunction.

The pneumatic connector 150 is particularly advantageous in microfluidic control system environments utilizing automation. As noted above, in this embodiment, the microfluidic plate 100 comprises an SBS-compliant 96 well format, and thus various "off-the-shelf" machines can be used to create an automated system. In one embodiment, an automated system includes a robotic arm or plate handler that moves the microfluidic plate 100 to a particular station. The microfluidic plate 100 may be already prepared and include the pneumatic manifold 120; however in certain embodiments, the automated system may dispense liquids into the wells of the plate 100 and also introduce the pneumatic manifold 120. The pneumatic connector 150 would then be mechanically introduced by to the pneumatic interface 134. Activating the vacuum line then automatically secures the pneumatic connector 150 to the pneumatic interface 134, establishing a secure, vacuum-held connection without any external or manual intervention. This feature has a significant advantage over connectors that use mechanical attachment or clamping means. Further, the pneumatic connector 150 presents a reliable and repeatable connector directly at a point of connection of the pneumatic manifold 120.

As noted above, the vacuum holding area 154 and seals 158 physically separate each gas line. However, pressure leakage may still occur due to a misaligned, broken, or otherwise incomplete seal. If unnoticed, this pressure leakage may lead to incorrect pressures being applied to each channel 122, potentially biasing the results of an experiment being performed on the microfluidic plate 100. One advantage of using a removable pneumatic connector 150 is that any incomplete seals resulting in pressure leakage between gas lines can be recognized as an aberration in vacuum pressure within the vacuum holding area 154. In certain embodiments, the controller 40 and/or computer 60 are configured to recognize deviations in pressure within the vacuum holding area 154 and report this information, e.g., via an alert or other means, to an operator. Thus, the operator may then take corrective action, such as reseating the pneumatic connector 150, to ensure a positive seal.

B. Second Embodiment of a Removable Pneumatic Connector

As noted above, the tubing 30 of FIG. 1 may also be removable from the controller 40 by a variety of means. For example, at the interface between the tubing 30 and controller 40, a variety of attachment means may be used, such as pneumatic, magnetic, mechanical attachment, and the like. FIGS. 12A-14 illustrate another embodiment of a removable pneumatic connector 200 according to the disclosure. The pneumatic connector 200 may be positioned between the tubing 30 and the controller 40, and may be configured to removably secure the pneumatic connector 200 to the controller 40. Further, in this embodiment, the pneumatic connector 200 further comprises in-line filters, which may be used to allow the passage of gas, but prevent fluid flow.

Figure 12A:
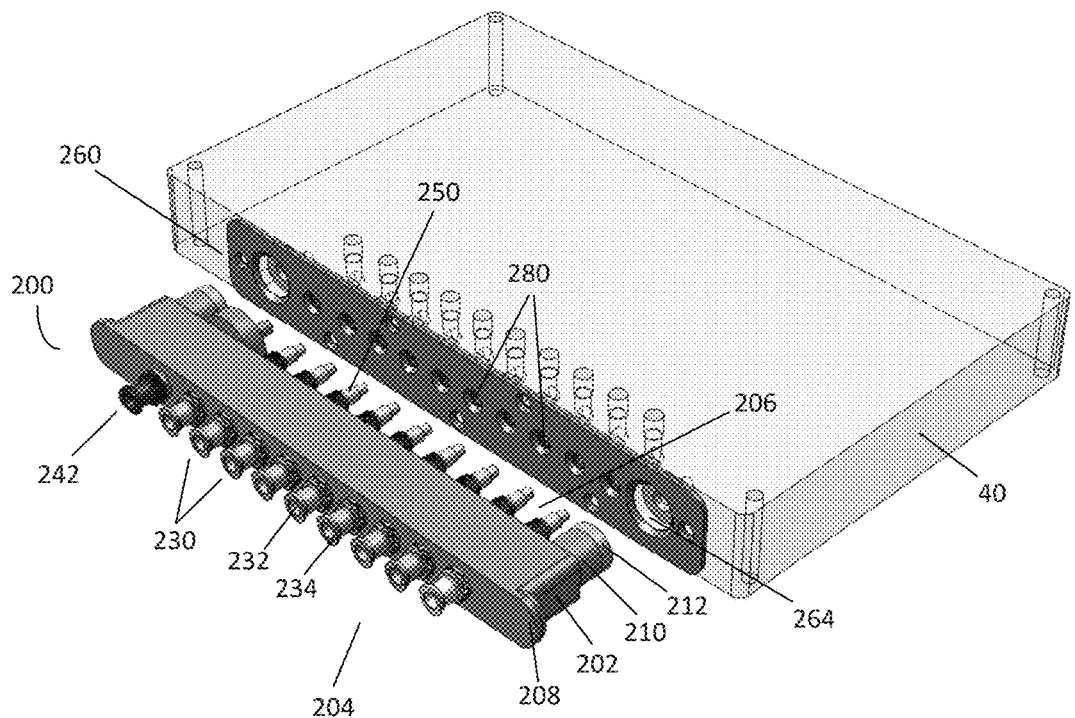
FIGS. 12A-B are perspective views of another embodiment of a pneumatic connector according to the disclosure in the disengaged and engaged states, respectively.
Figure 12B:
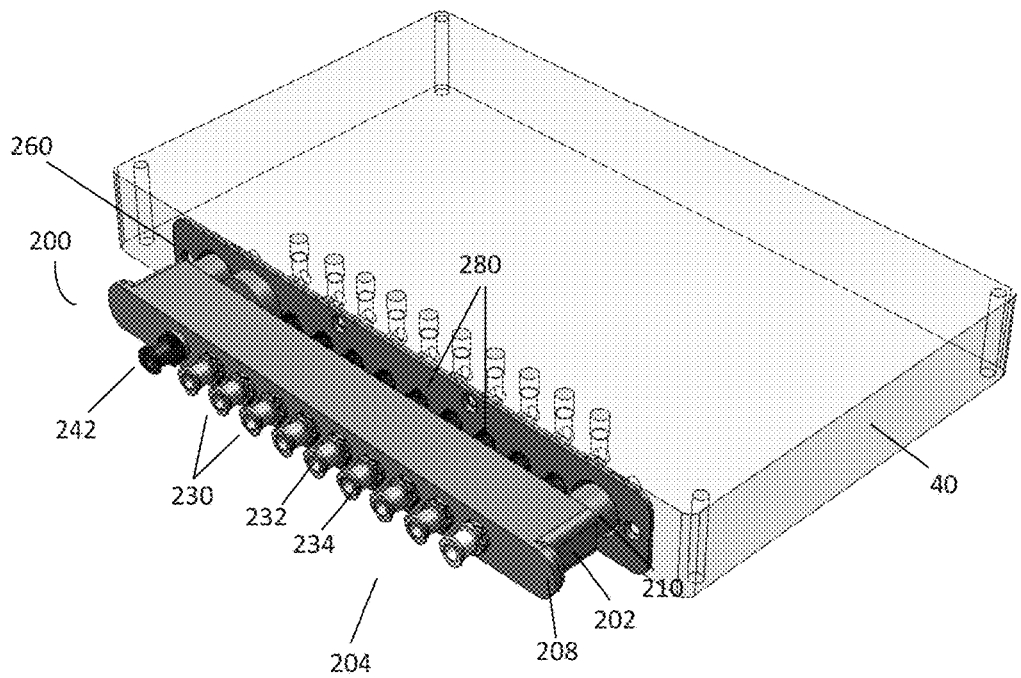

As shown in the embodiment of FIGS. 12A-B, the connector 200 may comprise a housing 202. The housing 202 may comprise clear PDMS, molded plastic, or another appropriate material. The housing 202 further comprises a tubing end 204 and an engagement end 206. A plurality of male ports 230 are disposed within and pass laterally through the housing 202 such that each male port 230 extends from both the tubing end 204 and the engagement end 206. On the tubing end 204, each male port 230 comprises a barb 234 for interfacing with a gas line, such as the gas lines comprising the tubing 30 of FIG. 1. To place the male port 230 in communication with a tubing, a corresponding gas line of the tubing is placed over the barb 234. While in this embodiment, the gas lines of the tubing 30 are secured using the barb 234, other forms of connection for gas lines may be used, such as TC connections, Luer connections, and the like.

On the engagement end 206, each male port 230 further comprises a stepped section 250 which is configured to engage with a corresponding female port 280 in an interface 260 on a pneumatic controller, such as the controller 40 of FIG. 1. Further, the male ports 230 comprise a channel 232 extending from the barb 234 to the stepped section 250, which may allow for the passage of gas, liquid, or other substances between the tubing 30 and controller 40. At least one of the male ports 230 may be designated for a particular function, such as a vacuum port 242. Further, a pair of tabs 208 extend laterally from each side of the housing 202 on the tubing end 204. The tabs 208 may be used, for example, for gripping the connector 200 to engage or disengage the connector 200 from the corresponding interface 260, which may be performed either manually, or by automation with appropriately configured hardware.

The housing 202 may further comprise a post 210 comprising a connector magnet 212 positioned on the engagement end 206. In this embodiment, the housing 202 comprises two posts 210 at each side of the male ports 230, each post 210 comprising a connector magnet 212. However, in certain embodiments, the housing 202 may comprise a single post, multiple posts, lack a post, or include posts without magnets. Similarly, in certain embodiments, the housing 202 may comprise a single magnet, multiple magnets, lack a magnet, or include magnets without posts. In the embodiment shown, the connector magnets 212 are shaped similarly to the attached surface of the post 210; however, a variety of magnets and shapes may be used.

Figure 13A:
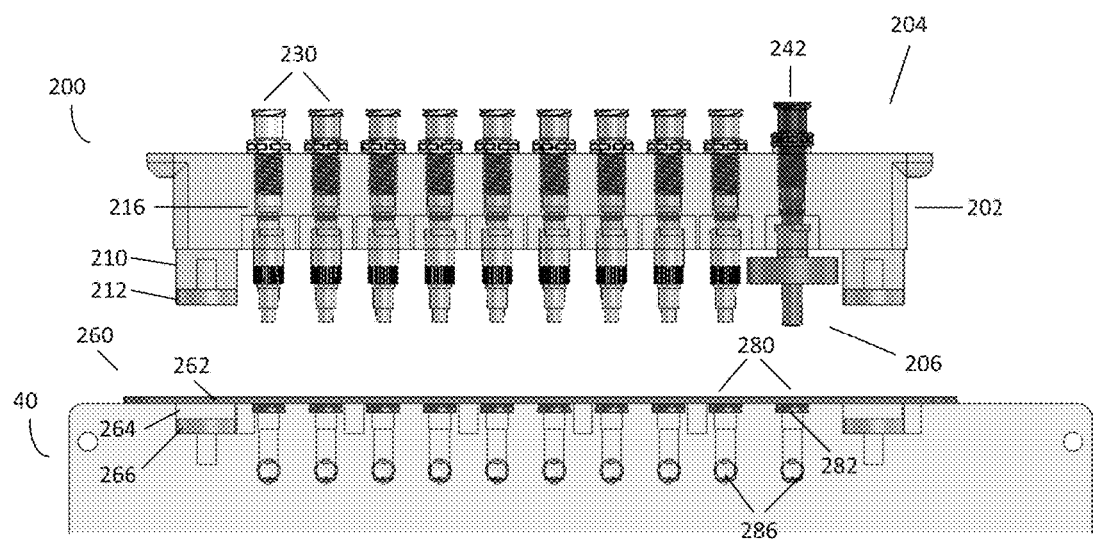
FIGS. 13A-B are front views of the pneumatic connector of FIGS. 12A-B in the disengaged and engaged states, respectively.

In the embodiment shown, each post 210 and connector magnet 212 are shaped to be received by a corresponding aperture 264 containing a receiving magnet 266 in the interface 260. An attractive force between each connector magnet 212 and receiving magnet 266 may be used to secure the connector 200 to the interface 260, thus placing the male ports 230 in fluid communication with the female ports 280. Further, the magnets 212, 266 may be used to help properly align and place the connector 200 over the interface 260. For example, the polarity of the connector magnets 212 may be configured to be the same as the polarity of the receiving magnets 266 when the connector 200 is positioned over the interface 260 backwards or in an otherwise incorrect position, thus resulting in a resistive force preventing the connector 200 from engaging with the interface 260. However, in certain embodiments, either the connector magnets 212 or receiving magnets 266 may simply comprise a piece of metal. In these embodiments, if proper alignment is desired, other forms of engagement may be used, e.g. by keying or spacing the placement of the male ports 230 and female ports 280 such that the connector 200 may only engage with the interface 260 in a single position. For example, as shown in FIG. 13A, the spacing between the vacuum port 242 and adjacent male port 230 may be slightly wider than the spacing between the other male ports 230. Similarly, in certain embodiments, the size and/or shape of the apertures 264 may vary compared to one another to accept only a particular post 210 and/or connector magnet 212 on a connector 200. Various embodiments and configurations are within the scope of the present disclosure.

In certain embodiments, other forms of securing engagement, as opposed to magnetic force, may be used to secure the connector 200 to the interface 260. For example, the connector 200 may use an existing in-line vacuum force, as in the connector 150 of FIG. 8, to pneumatically secure the connector to the interface. Alternately, other mechanical means may be used to secure the connector 200 to the interface 260, such as screws, thumb screws, bolts, and the like. For example, thumb screws may be preferable in some embodiments, as it provides a reliable connection between the connector 200 and interface 260 that is less likely to be accidentally dislodged. However, in embodiments using automation, pneumatics and/or magnetic coupling may be preferable, as less force is needed to disengage and engage the connector 200.

Figure 13B:
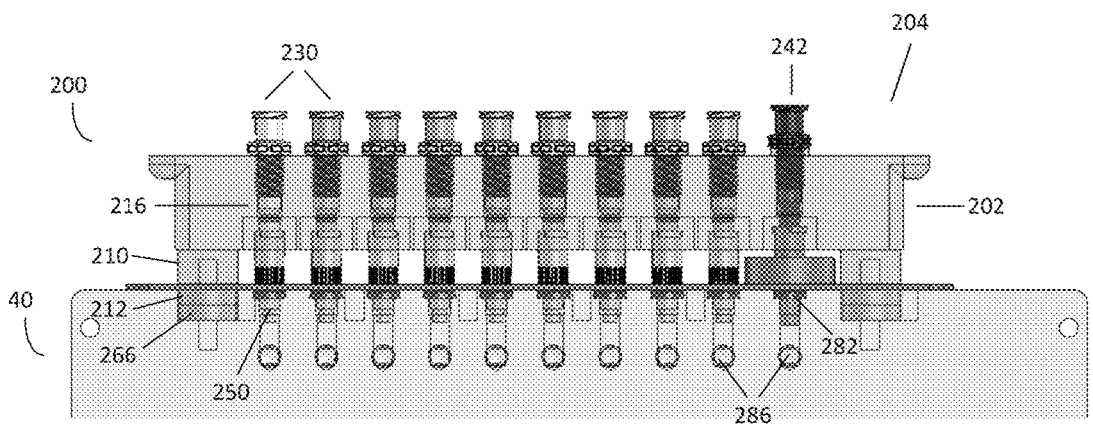
Figure 14:
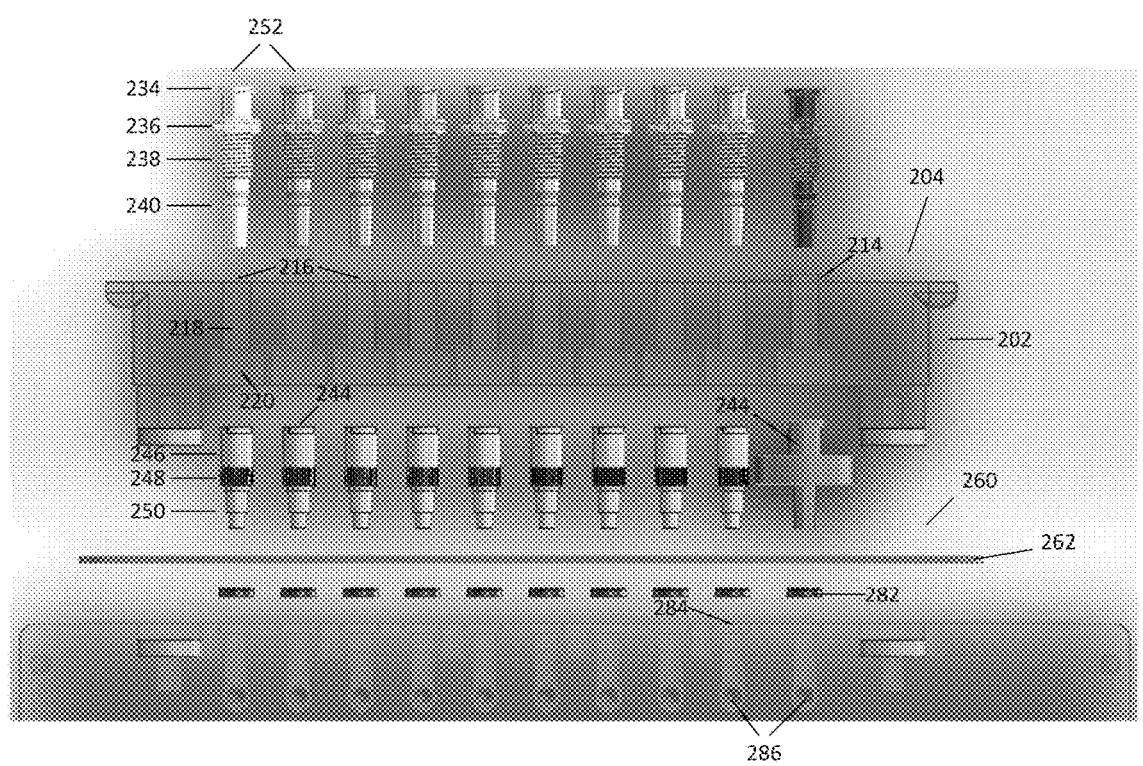
FIG. 14 is an exploded front view of the removable pneumatic connector of FIGS. 12A-B.

Referring to FIGS. 13A-B and FIG. 14, in this embodiment, the housing 202 further comprises a plurality of bores 216 passing through the housing 202, such that the bores 216 are open to the tubing end 204 and the engagement end 206. Each bore 216 may further comprise a fitting section 218 for receiving and securing one of the male ports 230 to the bore 216, and an open section 220 proximate the engagement end 206. In certain embodiments, the fitting section 218 may comprise additional features for receiving and securing a male port 230, such as threads, grooves, tapering, and the like. In the embodiment shown, the fitting section 218 has a thinner diameter than the open section 220, and the fitting section 218 and open section 220 are axial with respect to one another. Further, a bore 216 may be intended for a particular function, such as vacuum, for the vacuum port 242. This intention may be designated on the housing 202 by a structural feature or indicator 214, such as a raised surface on the tubing end 204. Alternately, the housing 202 may use other features, such as markings on the tubing end 204 or a keyed spacing or arrangement of ports, to designate the use of bores and ports for a particular function. In the embodiment shown, the vacuum port 242 is also colored differently from the male ports 230 as an indication of its intended use.

In the embodiment shown, the plurality of male ports 230 are positioned within the bores 216. Each male port 230 may comprise two separate pieces, a syringe 252 and a filter 244, which are configured to engage with one another to form the male port 230. When engaged together, the channel 232 (as shown in FIGS. 12A-B) extends through the syringe 252 and filter 244. In this embodiment, the syringe 252 and filter 244 each may comprise a body having several components. The syringe 252 comprises the barb 234, a bolt 236, a threaded segment 238, and a tapered segment 240. To position the syringe 252 within one of the bores 216, the tapered segment 240 is placed within the fitting section 218 via the tubing end 204 of the housing 202. The syringe 252 is then rotated by gripping the bolt 236, causing the threaded segment 238 to engage with the inner surface of the fitting section 218. The syringe 252 is properly positioned within the bore 216 when the bolt 236 is in contact with the surface of the tubing end 204, thus securing the syringe 252 within the bore 216.

While in this embodiment, the syringe 252 and filter 244 are separable, in certain embodiments, these elements may comprise a single component. Further, while the barb 234, bolt 236, threaded segment 238, and tapered segment 240 are arranged in this order along the syringe 252, these elements may be arranged in alternate ways to accommodate alternate embodiments of bores 216 and/or housings 202 according to the disclosure. For example, in certain embodiments, a bolt 236 may be placed below a threaded segment 238 so that the syringe 252 may be positioned within the bore 216 from the engagement end 206. Similarly, in certain embodiments, the threaded segment 238 may comprise other features, such as grooves or tapering, for securing the syringe 252 within the bore 216. In still further embodiments, the various features of the syringe 252 and filter 244 may be molded as part of the housing 202, for example, such that the channel 232 is an integral component of the housing 202. Various embodiments are considered to be within the scope of the disclosure.

As noted above, each male port 230 may comprise two separate pieces, a syringe 252 and a filter 244. The filter 244 may be configured to engage with the syringe 252, for example, by using a Luer-style connection (such as a Luer slip or Luer lock), threads, or other form of engagement. In this embodiment, the filter 244 comprises a receiving section 246, a filter element 248 disposed within the channel 232, and the stepped section 250. The portion of the channel 232 within the receiving section 246 may be tapered to receive the tapered segment 240 of the syringe 252. Thus, to secure the filter 244 to the syringe 252, the filter 244 is positioned within the open section 220 of the bore 216 such that the receiving section 246 of the filter 244 receives the tapered segment 240 of the syringe 252. The filter 244 is then pressed against the syringe 252, securing the filter 244 to the syringe 252 by friction and creating a fluid tight seal.

In this embodiment, the filter 244 comprises the filter element 248 disposed within the channel 232. The filter element 248 may comprise any kind of filter, such as hydrophobic filters and PTFE filters. In this way, the filters 244 may allow passage of air and other gases, but prevent the passage of water and other fluids. The size, shape, and kind of filters 244 may also vary depending on a desired flow rate or other parameters. For example, in this embodiment, the filters 244 comprise nine 4 mm 0.45 µm PTFE filters and one 13 mm 0.45 µm PTFE filter. The single 13 mm diameter filter may be used for a vacuum line connected to the vacuum port 242, which may benefit from a higher air flow rate. Filters may comprise, for example, Millex® syringe filters, commercially available from EMD Millipore Corporation. However, in certain embodiments, a filter 244 may lack a filter element 248, and thus allow passage of either gas or liquid.

In this embodiment, the filters 244 are replaceable. In some embodiments, filters may be replaced by ejecting each of the filters 244 and replacing them with a new set. In certain embodiments, filters may be replaced by ejection and replacement with a new set, e.g., using mechanical means. Similarly, in certain embodiments, filters 244 may be simultaneously attached, e.g., by placing the connector 200 onto an array of filters 244 appropriately spaced to receive each of the tapered portions of the corresponding syringes. However, in still further embodiments, filters 244 may be permanently connected to a connector 200. Various embodiments and configurations are considered to be within the scope of the disclosure.

The connector 200 is configured to engage with a corresponding interface 260, which may be located on either side of the tubing 30, such as on a manifold or controller. For example, a controller, such as the controller 40 of FIG. 1, may further comprise an interface 260 configured to receive the connector 200. In the embodiment shown in FIGS. 13A-B and FIG. 14, the interface 260 comprises a plurality of female ports 280 which receive the male ports 230 of the connector 200, placing the female ports 280 and male ports 230 in fluid communication. Each female port 280 comprises a seal 282 positioned above an opening 284 in communication with a channel 286 of the pneumatic controller 40. Each channel 286 may be configured to supply a liquid, gas, or other substance to the female ports 280. In the embodiment shown, each channel 286 is configured to supply variable pneumatic pressure from the controller 40. Accordingly, when the male ports 230 of the connector 200 are in communication with the female ports 280 of the interface 260, the channel 232 of the male port 230 is in communication with the channel 286 of the controller 40. Accordingly, the tubing 30 is in fluid communication with the channels 286 of the controller 40 via the connector 200.

Seals 282 are used to fluidly separate each female port 280, and accordingly each channel 286, from one another. The seals 282 may be retained by a panel 262. In the embodiment shown, the panel 262 comprises openings for each of the female ports 280 and apertures 264. In certain embodiments, the seals 282 may be positioned within grooves defined within the openings 284 of the female port 280, which may either complement or replace the panel 262. Seals 282 may comprise, for example, O-rings, which may further comprise a "U"-shaped cross-section to allow for low insertion force.

In the embodiment shown in FIGS. 12A and 13A, the connector 200 may be initially separated and disengaged from the interface 260 on the controller 40. As shown in the embodiments of FIGS. 12B and 13B, the connector 200 is engaged with the interface 260 when the engagement end 206 is brought into contact with the interface 260 such that the post 210 with the connector magnet 212 enters the corresponding aperture 264 with the receiving magnet 266, thus using magnetic attraction to secure the connector 200 to the interface 260. Engaging the connector 200 to the interface 260 further causes each male port 230 to enter a corresponding female port 280, thus placing each gas line of the tubing 30 in fluid communication with the channels 286 of the controller. Further, each seal 282 is placed in contact with the stepped section 250 of the corresponding filter 244, substantially preventing fluid communication between each channel 286. Thus, the controller 40 can supply precise levels of variable pressure, including vacuum, to a corresponding manifold downstream to control a microfluidic process or experiment in a microfluidic plate.

Similar to the pneumatic connector 150, the pneumatic connector 200 results in a variety of advantages, such as ease of cleaning, transportation of a manifold and tubing, reducing operator workflow, applicability to automation, and identification of incomplete or imperfect seals. Additionally, the use of a plurality of filters 244 in a single connector 200 has a significant advantage in that all of the filters 244 may be simultaneously removed from the controller concurrent with disengaging the connector, as opposed to individually removing each filter. Thus, the connector 200 provides a fast, nearly automatic connection to the controller.

Moreover, the use of filters 244, such as hydrophobic filters, in the removable connector 200 between the tubing 30 and controller 40 has additional advantages. For example, if a liquid backflows from the manifold 120 through the tubing 30, filters 244 prevent the liquid from entering the channels 286, potentially harming or contaminating the controller 40. Filters 244 may also be used to prevent contamination of the tubing 30 and a downstream manifold and microfluidic plate, such as the microfluidic plate 100 and manifold 120 attached to the tubing 30 of FIGS. 4A-B. Moreover, filters 244 using a slip, threaded, or other form of removable connection may be single-use, helping to prevent contamination each time the connector 200 is secured to the interface 260 of the controller 40.

A connector 200 incorporating a plurality of filters 244 may also be used for efficiently cleaning both the manifold 120 and tubing 30. Conventional cleaning methods of the gas lines and tubing associated with pneumatic control of microfluidic devices typically involve aspirating a cleaning solution into a syringe, and then injecting the cleaning solution into individual lines. In contrast, the controller 40 may be configured to aspirate a cleaning solution, such as hydrogen peroxide, into the tubing 30, thus cleaning all of the gas lines comprising the tubing 30 simultaneously.

Microfluidic Cleaning Plate and Method of Use

Figure 15:
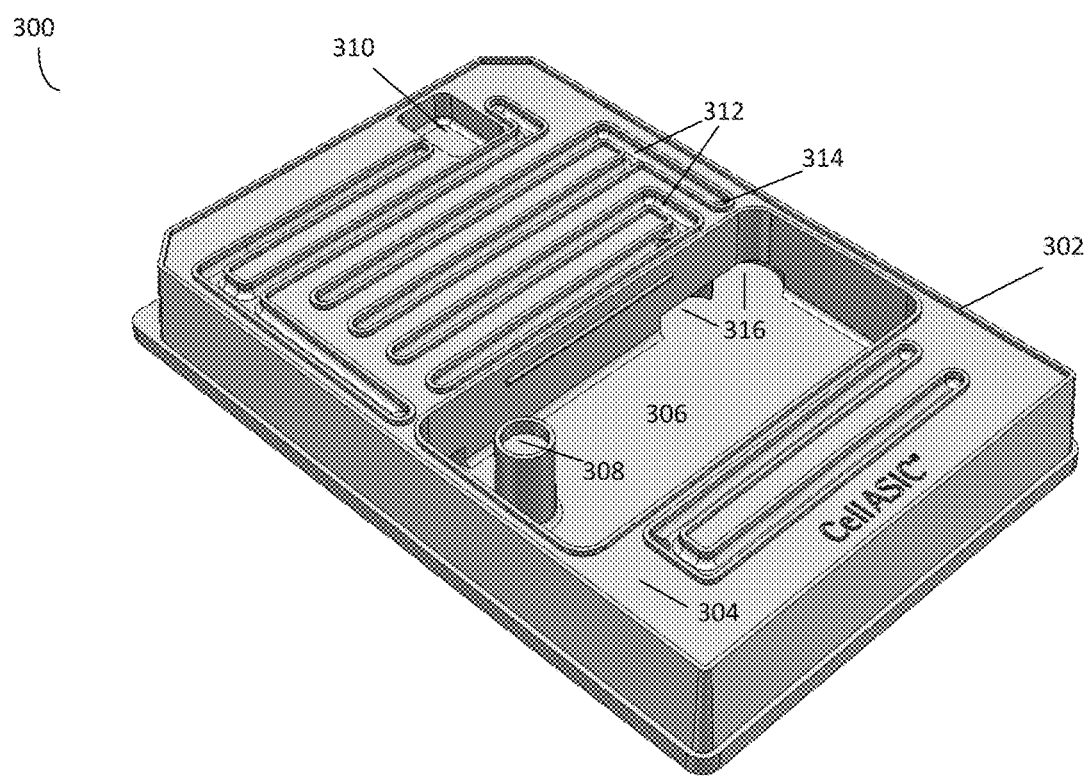
FIG. 15 is a perspective view of an embodiment of a cleaning plate according to an embodiment of the disclosure.
Figure 16:
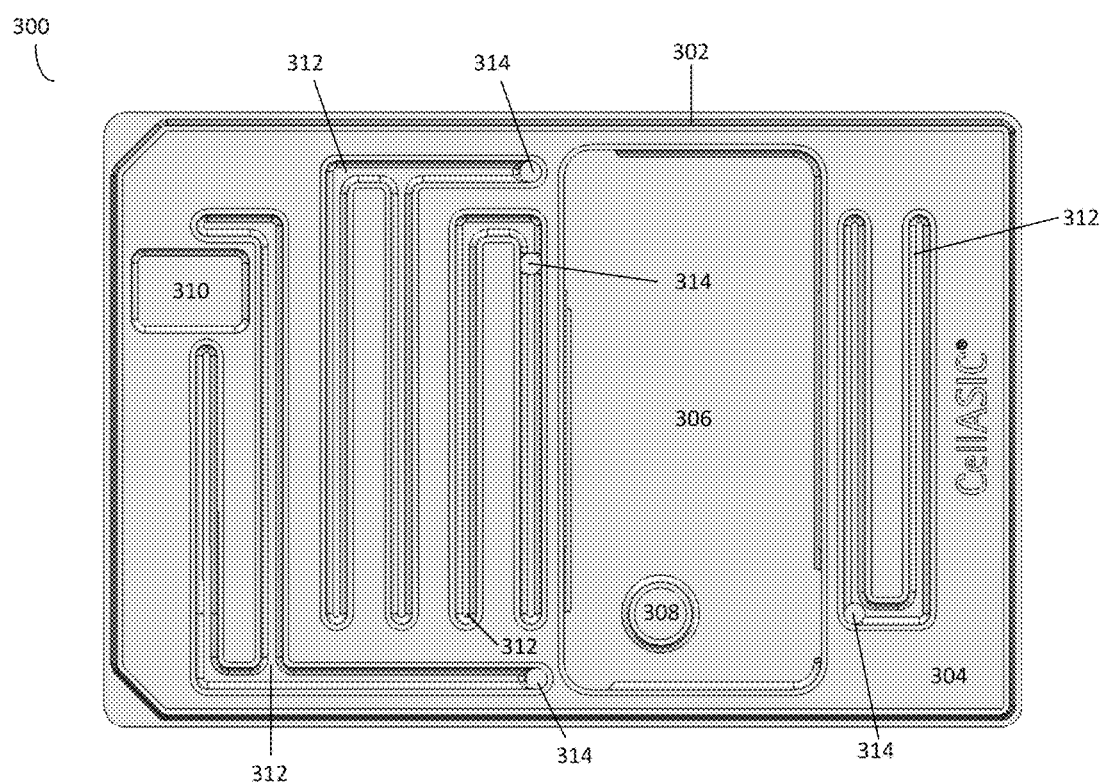
FIG. 16 is a top view of the cleaning plate of FIG. 15.
Figure 17:
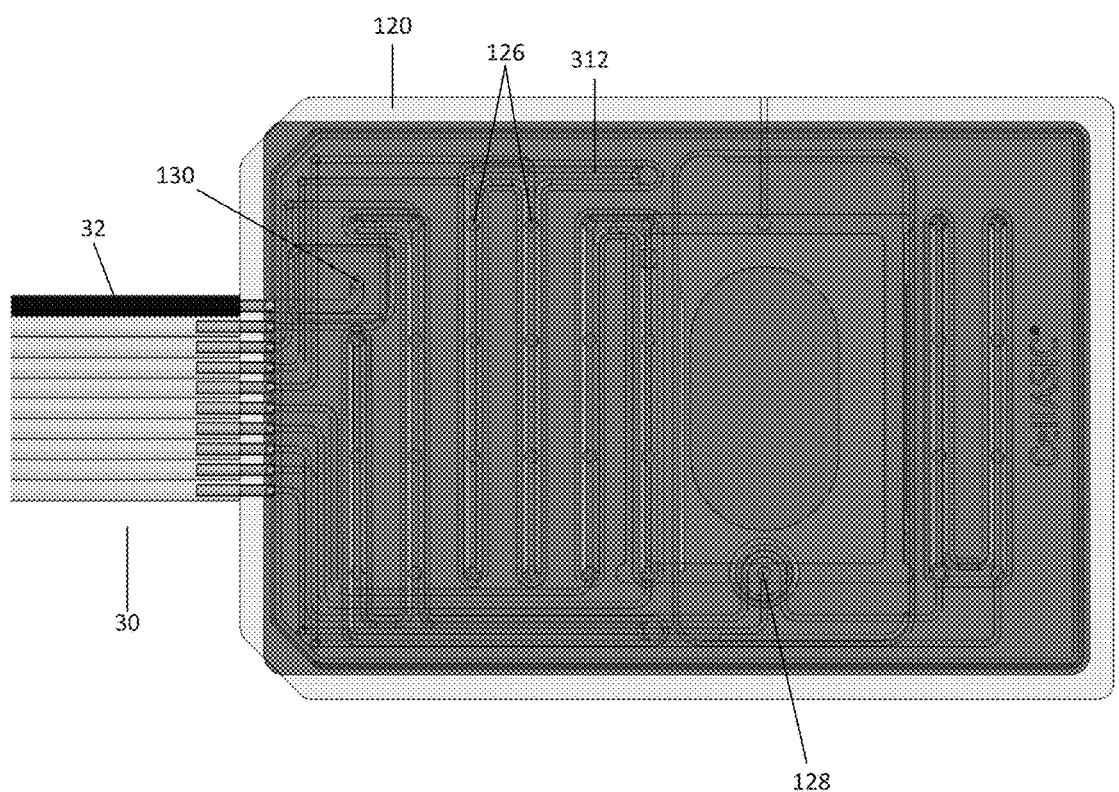
FIG. 17 is a top view of a pneumatic manifold positioned over the cleaning plate of FIG. 15.

FIGS. 15-17 illustrate a cleaning plate 300 for cleaning a manifold and tubing according to an embodiment of the disclosure. The cleaning plate 300 may comprise a variety of materials, such as PDMS, molded plastic, and the like. The cleaning plate 300 has similar dimensions to a corresponding microfluidic plate, such as the microfluidic plate 100 of FIG. 2. Accordingly, in the embodiment shown in FIG. 17, a manifold, such as the manifold 120 of FIGS. 4A-B, may be positioned over the cleaning plate 300 such that it is in fluid communication with the cleaning plate 300, just as the manifold 120 would be positioned over and enter fluid communication with a microfluidic plate 100. Further, a controller may deliver vacuum to the cleaning plate 300 via a vacuum channel to seal the manifold to the plate.

In the embodiment shown in FIGS. 15-16, the cleaning plate 300 further comprises sidewalls 302 that are raised from a surface 304 of the cleaning plate 300. The sidewalls 302 come into contact with the manifold when the manifold is sealed to the plate. The cleaning plate 300 may comprise a plurality of wells, which in the embodiment shown comprise a central well 306, gas line well 308, and vacuum line well 310. The central well 306 and gas line well 308 may be filled with a cleaning solution, such as a hydrogen peroxide solution, an alcohol solution, and the like. The cleaning plate 300 further comprises a plurality of cleaning solution channels 312. In the embodiment shown in FIG. 17, which illustrates the manifold 120 of FIG. 5 aligned over the cleaning plate 300 of FIG. 16, the gas line well 308 and vacuum line well 310 are positioned beneath the outlets for the gas environment channel 128 and vacuum channel 130 of the manifold 120, respectively. Similarly, the cleaning solution channels 312 are positioned beneath the channel outlets 126 of the manifold. Referring to FIGS. 15-16, the cleaning solution channels 312 further comprise openings 314, which are in fluid communication with a plurality of transfer channels 316 in fluid communication with the central well 306. In this embodiment, the transfer channels 316 comprise four cavities in the base of the central well 306 and an internal channel (not shown) rising up from the base and in communication with the openings 314 within the cleaning solution channels 312.

In this embodiment, the sidewalls of the central well 306, gas line well 308, and cleaning solution channels 312 rise to the same height as the sidewalls 302 of the cleaning plate 300, and thus are fluidly separated from one another when the manifold 120 is sealed to the plate. In contrast, the sidewalls of the vacuum line well 310 only rise to the surface 304 of the plate. Thus, to seal a manifold to the cleaning plate 300 (in the embodiment shown in FIG. 17), the manifold is aligned over and placed on top of the plate and pressed down against the plate. A vacuum line in communication with the manifold 120 is then activated. Activating the vacuum line seals the manifold 120 to the plate by creating a vacuum in the volume between the surface 304, sidewalls 302, and the sidewalls of the central well 306, gas line well 308, and cleaning solution channels 312.

Once the manifold 120 has been sealed to the cleaning plate 300, a cleaning sequence may be performed which aspirates cleaning solution placed in the wells of the cleaning plate 120 into the manifold and the tubing between the manifold 120 and the controller, such as the controller 40 of FIG. 1. First, the central well 306 and gas line well 308 may be filled with a cleaning solution. The manifold 120 is then placed over the cleaning plate 300, and a cleaning protocol may be activated on the controller 40. The controller delivers negative pressure to each of the channels within the manifold 120. The negative pressure aspirates cleaning solution from the central well 306 into the transfer channels 316, through the cleaning solution channels 312, and into the outlets 126 of the manifold. Similarly, cleaning solution from the gas line well 308 is aspirated into the outlet for the gas environment channel 128 of the manifold. As the cleaning solution traverses the channels of the manifold 120, the cleaning solution continues into the tubing 30, thus cleaning each of the gas lines comprising the tubing 30. Finally, the cleaning solution is stopped by the filter 244 of the connector 200 (as shown in the embodiment of FIGS. 12A-B), thus maximizing cleaning of the length of the tubing 30, manifold 120, and any intermediate components. Further, because the filter 244 stops the flow of the cleaning solution, the connector 200 also minimizes any risk of damage to the controller 40 as a result of the cleaning protocol.

Once the cleaning process is complete, it may be reversed such that the cleaning solution is returned back into the cleaning plate 300. The manifold 120 may then be disconnected from the cleaning plate 300. The manifold is then ready to use for attachment to a microfluidic plate for an experiment. If the filters 244 of the connector 200 are single-use, they may be replaced.

Further, it should be noted that various features of the above embodiments and disclosure may be combined with one another to form various pneumatic connectors, pneumatic manifolds, microfluidic plates, cleaning plates, and microfluidic control and analysis systems. The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings.

Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A removable pneumatic connector, comprising:
    a body having a plurality of bores passing through, each bore surrounded by a sealing member on an inner surface of the body;
    a vacuum port disposed on the inner surface of the body; and
    an outer seal on the inner surface of the body surrounding the sealing members and the vacuum port;
    wherein the outer seal and each of the sealing members are configured to create a vacuum holding area in the volume between the outer seal and each of the holding members when the inner surface of the body is placed against a substrate.

2. The removable pneumatic connector of claim 1, further comprising a plurality of gas lines, wherein each line of the plurality of gas lines is placed within a corresponding bore.

3. The removable pneumatic connector of claim 2, further comprising a vacuum line placed within the vacuum port.

4. The removable pneumatic connector of claim 3, wherein the vacuum line is configured to deliver negative pressure to the vacuum port, such that a vacuum is created within the vacuum holding area.

5. The removable pneumatic connector of claim 1, wherein the sealing member surrounding each bore and the outer seal have a similar compressibility ratio.

6. The removable pneumatic connector of claim 1, wherein the sealing member surrounding each bore comprises an O-ring, and the outer seal comprises a gasket.

* * * * *